US010676747B2

(12) United States Patent
Rosenblum et al.

(10) Patent No.: US 10,676,747 B2
(45) Date of Patent: Jun. 9, 2020

(54) METHODS FOR IMPROVING COGNITIVE FUNCTION VIA MODULATION OF QUINONE REDUCTASE 2

(71) Applicant: Carmel-Haifa University Economic Corp. Ltd., Haifa (IL)

(72) Inventors: Kobi Rosenblum, Haifa (IL); Akiva Rappaport, Haifa (IL)

(73) Assignee: CARMEL-HAIFA UNIVERSITY ECONOMIC CORP. LTD., Haifa (IL)

( * ) Notice: Subject to any disclaimer, the term of this patent is extended or adjusted under 35 U.S.C. 154(b) by 0 days.

(21) Appl. No.: 16/173,959

(22) Filed: Oct. 29, 2018

(65) Prior Publication Data

US 2019/0119684 A1 Apr. 25, 2019

Related U.S. Application Data

(62) Division of application No. 15/126,291, filed as application No. PCT/IL2015/050284 on Mar. 18, 2015, now Pat. No. 10,113,171.
(60) Provisional application No. 61/954,687, filed on Mar. 18, 2014.

(51) Int. Cl.

| | | |
|---|---|---|
| *C12N 15/113* | (2010.01) | |
| *A61K 31/7105* | (2006.01) | |
| *A61K 31/713* | (2006.01) | |
| *A61K 31/165* | (2006.01) | |
| *A61K 31/404* | (2006.01) | |
| *A61K 31/4045* | (2006.01) | |
| *A61K 31/4375* | (2006.01) | |
| *A61K 31/455* | (2006.01) | |
| *A61K 31/7064* | (2006.01) | |
| *A61K 31/255* | (2006.01) | |

(52) U.S. Cl.
CPC ........ *C12N 15/1137* (2013.01); *A61K 31/165* (2013.01); *A61K 31/255* (2013.01); *A61K 31/404* (2013.01); *A61K 31/4045* (2013.01); *A61K 31/4375* (2013.01); *A61K 31/455* (2013.01); *A61K 31/7064* (2013.01); *A61K 31/713* (2013.01); *A61K 31/7105* (2013.01); *C12Y 106/05005* (2013.01); *C12N 2310/14* (2013.01); *C12N 2310/531* (2013.01)

(58) Field of Classification Search
CPC .... C12N 15/1137; C12N 15/63; C12N 15/86; C12N 2310/14
See application file for complete search history.

(56) References Cited

U.S. PATENT DOCUMENTS 7,749,973 B2 * 7/2010 Sarkis .................. C07K 14/005
424/93.1
2005/0182125 A1 8/2005 Lockhart et al.
2006/0178328 A1 8/2006 Kaemmerer
2015/0148401 A1 5/2015 Toyoshima et al.

FOREIGN PATENT DOCUMENTS

| WO | WO 2002/038141 A2 | 5/2002 | |
|---|---|---|---|
| WO | WO 2008/013764 A2 | 1/2008 | |
| WO | 2008/144455 A1 | 11/2008 | |
| WO | WO-2013023084 A2 * | 2/2013 | ............. A61K 31/00 |

OTHER PUBLICATIONS

Chomarat et al. Biochimie 89 1264-1275 (Year: 2007).*
Bailey, C. H., et al., Toward a Molecular Definition of Long-term Memory Storage, Proc Natl Acad Sci USA 93(24):13445-3452, 1996.
Belinson, H., et al., Activation of the Amyloid Cascade in Apolipoprotein E4 Transgenic Mice Induces Lysosomal Activation and Neurodegeneration Resulting in Marked Cognitive Deficits, Journal of Neuroscience 28(18):4690-4701, Apr. 30, 2008.
Benoit, C-E., et al., Loss of Quinone Reductase 2 Function Selectively Facilitates Learning Behaviors, The Journal of Neuroscience 30(38)12690-12700, 2010.
Boehm-Cagan, A., and D.M. Michaelson, Reversal of apoE4-Driven Brain Pathology and Behavioral Deficits by Bexarotene, Journal of Neuroscience 34(21):7293-7301, May 21, 2014.
Brouillette, J., and R. Quirion, Transthyretin: A Key Gene Involved in the Maintenance of Memory Capacities During Aging, Neurobiology of Aging 29(11):1721-1732, 2008.
Brouillette, J., et al., Hippocampal Gene Expression Profiling Reveals the Possible Involvement of Homer 1 and GABAB Receptors in Scopolamine-Induced Amnesia, J. Neurochemistry 102(6):1978-1989, 2007.
Bureš, J., et al., Conditioned Taste Aversion: Memory of a Special Kind, Oxford University Press, 1998.
Buryanovskyy, L., et al., Crystal Structure of Quinone Reductase 2 in Complex with Resveratrol, Biochemistry 43(36):11417-11426, 2004.
Ferry, G., et al., Old and New Inhibitors of Quinone Reductase 2, Chemico-Biological Interactions 186(2):103-109, 2010.
Fitzpatrick, J., Inhibition of Quinone Oxidoreductase 2 Improves Learning in a Mouse Model of Vascular Dementia, Neurology 82(10)(Suppl):p. 1-237, 2014.
Graves, P.R., et al., Discovery of Novel Targets of Quinoline Drugs in the Human Purine Binding Proteome, Mol Pharmacol 62:1364-372, 2002.
Harada, S., et al., An Association Between Idiopathic Parkinson's Disease and Polymorphisms of Phase II Detoxification Enzymes: Glutathione S-Transferase MI and Quinone Oxidoreductase 1 and 2, Biochemical and Biophysical Research Communications 288(4):887-92, 2001.

(Continued)

*Primary Examiner* — Brian Whiteman
(74) *Attorney, Agent, or Firm* — Knobbe, Martens, Olson & Bear LLP

(57) ABSTRACT

An active agent capable of reducing quinone reductase 2 activity is for use in improvement of cognition in a subject. Such an active agent can be a nucleic acid molecule that reduces the gene expression level of quinone reductase 2 or an inhibitor of quinone reductase 2 activity. A pharmaceutical composition can contain the active agent or a vector containing the active agent.

6 Claims, 11 Drawing Sheets

Specification includes a Sequence Listing.

(56) References Cited

OTHER PUBLICATIONS

Harada, S., et al., A Possible Association Between an Insertion/deletion Polymorphism of the NQO2 Gene and Schizophrenia, Psychiatric Genetics 13(4):205-09, 2003.

Hashimoto, T., and M. Nakai, Increased Hippocampal Quinone Reductase 2 in Alzheimer's Hashimoto, Tetsuya, and Masami Nakai. Increased Hippocampal Quinone Reductase 2 in Alzheimer's Disease, Neuroscience Letters 502(1):10-12, 2011.

Iskander, K., Deficiency of NRH: Quinone Oxidoreductase 2 Increases Susceptibility to 7, 12-Dimethylbenz(a)anthracene and Benzo(a)pyrene-Induced Skin Carcinogenesis, Cancer Research 64(17) (2004):5925-928, 2004.

Jaiswal, A.K., Human NAD(P)H:quinone Oxidoreductase2. Gene Structure, Activity, and Tissue-Specific Expression, J Biol Chem 269(20):14502-4508, 1994.

Kwiek, J.J., et al., Kinetic Mechanism of Quinone Oxidoreductase 2 and Its Inhibition by the Antimalarial Quinolines, Biochemistry 43(15):4538-547, 2004.

Lois, C., Germline Transmission and Tissue-specific Expression of Transgenes Delivered by Lentiviral Vectors, Science 295(5556):868-72, 2002.

Long, D.J., and A.K. Jaiswal, NRH:quinone Oxidoreductase2 (NQO2), Chemico-Biological Interactions 129(1-2):99-112, 2000.

Mailliet, F., et al., Organs From Mice Deleted for NRH:quinone Oxidoreductase 2 Are Deprived of the Melatonin Binding Site MT3, FEBSLett 578:116-20, 2004.

Mailliet, F., et al., Characterization of the Melatoninergic MT3 Binding Site on the NRH:quinone Oxidoreductase 2 Enzyme, Biochem Pharmacol 1-2:74-88, 2005.

Meiri, N. and Kobi Rosenblum, Lateral Ventricle Injection of the Protein Synthesis Inhibitor Anisomycin Impairs Long-term Memory in a Spatial Memory Task, Brain Research 789(1):48-55, 1998.

Paxinos, G., and C. Watson, The Rat Brain in Stereotaxic Coordinates, Academic, Sydney, Australia, 1986.

Quinones, IUPAC Gold Book, N.P., N.D., accessed online Aug. 26, 2013.

Rosenblum, K., Conditioned Taste Aversion and Taste Learning: Molecular Mechanisms, Concise Learning and Memory: The Editor's Selection, Academic, Amsterdam, 2008.

Rosenblum, K., et al., Taste Memory: The Role of Protein Synthesis in Gustatory Cortex, Behavioral and Neural Biology 59(1):49-56, 1993.

Rosenblum, K., et al., Modulation of Protein Tyrosine Phosphorylation in Rat Insular Cortex After Conditioned Taste Aversion Training, Proceedings of the National Academy of Sciences 92(4):1157-161, 1995.

Sanderson, D.J., et al., The Role of Habituation in Hippocampus-Dependent Spatial Working Memory Tasks: Evidence From GluA1 AMPA Receptor Subunit Knockout Mice, Hippocampus 22:981-984, 2012.

Segev, Y., et al., ApoE $\epsilon 4$ Is Associated With eIF2$\alpha$ Phosphorylation and Impaired Learning in Young Mice, Neurobiology of Aging, 34:863-872, 2013.

Segev, Y., PKR Inhibition Rescues Memory Deficit and ATF4 Overexpression in ApoE $\epsilon 4$ Human Replacement Mice, The Journal of Neuroscience 35(38):12986-12993, 2015.

Tipps, M.E., et al., Delay and Trace Fear Conditioning in C57BL/6 and DBA/2 Mice: Issues of Measurement and Performance, Learning & Memory 21:380-393, 2014.

Tong, L.M., Inhibitory Interneuron Progenitor Transplantation Restores Normal Learning and Memory in ApoE4 Knock-In Mice Without or With A$\beta$ Accumulation 34(29)9506-9515, Jul. 16, 2014.

Vella, F., NRH:quinone Reductase 2: An Enzyme of Surprises and Mysteries, Biochemical Pharmacology 71(1-2):1-12, 2005.

Wang, W., and A. Jaiswal, Sp3 Repression of Polymorphic Human NRH:quinone Oxidoreductase 2 Gene Promoter, Free Radical Biology and Medicine 37(8):1231-243, 2004.

Vorhees, C.V., and M.T. Williams, Morris water maze: procedures for assessing spatial and related forms of learning and memory, Nat Protoc, 1(2):848-58, 2006.

Wu, Y., Neuroprotective Effects of Lithium on Scopolamine-Induced Amnesia Through Decreasing Quinone Reductase 2 in Rats, Alzheimer's & Dementia 8(4)p. 199-p. 200, 2012.

Antoine, M., et al., Characterization of cofactors, substrates and inhibitor binding to flavoenzyme quinone reductase 2 by automated supramolecular nano-electrospray ionization mass spectrometry, The Institution of Electrical Engineers, Stevenage, Great Britain, Feb. 15, 2012, and International Journal of Mass Spectrometry 312:87-96, 2012.

Cai, J.-B., et al., Negative regulation of quinone reductase 2 by resveratrol in cultured vascular smooth muscle cells, Clinical and Experimental Pharmacology and Physiology 35(12):1419-1425, 2008.

Chomarat, P., et al., Cellular knock-down of quinone reductase 2: A laborious road to successful inhibition by RNA interference, Biochimie 89(10):1264-1275, 2007.

Extended European Search Report received in International Patent Application No. PCT/IL2015050284, dated Nov. 10, 2017.

\* cited by examiner

METHODS FOR IMPROVING COGNITIVE FUNCTION VIA MODULATION OF QUINONE REDUCTASE 2

CROSS-REFERENCES TO RELATED APPLICATION

Any and all applications for which a foreign or domestic priority claim is identified in the Application Data Sheet as filed with the present application are hereby incorporated by reference under 37 CFR 1.57.

SEQUENCE LISTING IN ELECTRONIC FORMAT

The present application is being filed along with an Electronic Sequence Listing as an ASCII text file via EFS-Web. The Electronic Sequence Listing is provided as a file entitled 29280285_1.txt created and last saved on Oct. 23, 2018, which is approximately 3 kilobytes in size. The information in the Electronic Sequence Listing is incorporated herein by reference in its entirety in accordance with 35 U.S.C. § 1.52(e).

FIELD OF INVENTION

The present invention relates to methods for improving cognitive function by reducing the level of expression or activity of quinone reductase 2.

BACKGROUND OF THE INVENTION

Decline in cognitive function in ageing and neurodegenerative disease is a major health and social problem. Currently, the approach for improving cognitive function involves pharmacological intervention targeting neurotransmitter pathways believed to be involved in the process of memory formation with the aim of increasing neurotransmitter level and thus improve signal transmission.

Currently, drug therapies for cognitive impairment are at best symptomatic or supportive. Consequently, there is an unmet need for therapies and methods for treating cognitive impairment, a need that is steadily increasing with the ageing of the world population. The need for improving cognition is not a prerogative only of cognitively impaired patients but may also be desired by normally functioning individuals desiring to improve learning and memory.

SUMMARY OF INVENTION

In one aspect the present invention is related to an active agent capable of reducing quinone reductase 2 activity, for use in improvement of cognition in a subject. Contemplated active agents may reduce said quinone reductase 2 activity by decreasing the gene expression level of quinone reductase 2 or by inhibiting the enzymatic activity of quinone reductase 2.

In another aspect the present invention is related to a vector comprising an active agent that reduces the gene expression level of quinone reductase 2.

In yet another aspect the present invention provides a pharmaceutical composition comprising an active agent or a vector as defined herein and a pharmaceutically acceptable carrier.

In still another aspect the present invention provides a method for improving cognition in a subject in need thereof comprising administering to said subject an active agent capable of reducing the expression level of quinone reductase 2 (QR2).

In a further aspect the invention provides a method for improving cognition in a subject in need thereof comprising administrating to said subject an active agent reducing the quinone reductase 2 activity, wherein said subject is not treated with scopolamine.

BRIEF DESCRIPTION OF DRAWINGS

FIGS. 13A to 13D show levels of freezing response of mice injected with QR2 shRNA (n=10) or scrambled sequence (n=10) during the conditioned context test on day 2 and tone test on day 3, and a week later. FIG. 13A shows a significant difference in the freezing response of QR2 shRNA injected mice during the conditioned context exposure on day 2 (Context on day 2; t1 8=-2.344, p=0.031); freezing levels during the testing were averaged over one epoch of 10-min exposure to the conditioned context. FIG. 13B shows that freezing levels during the testing periods were averaged over five 10 s tone, and 210 s inter trial interval (ITI) periods. A significant difference between QR2 shRNA and scrambled sequence injected groups in the freezing responses during tone periods on day 3 (Tone period on day 3 t1 8=-3.481, p=0.003). FIGS. 13C and 13D show that responses to context in FIG. 13C and tone in FIG. 13D after 1 week, QR2 shRNA injected mice showed enhanced long term memory (context 1 week later; t1 8=-2.350, p=0.03, tone 1 week later; t1 8=-2.347, p=0.031 paired t-test). Data are represented as mean±SEM.

FIG. 14A shows that escape latencies in hidden-platform tests (four trials a day), plotted as a function of training days, are shorter for QR2 shRNA injected than scrambled injected mice. A repeated measures ANOVA with a Greenhouse-Geisser correction determined that mean scores for escape latency of QR2 shRNA injected mice were statistically different between training days (^(2.216, 19.947)=16.932, p<0.00003). Post hoc tests using the Bonferroni correction revealed that QR2 shRNA injected mice perform better on day3 to day4 of training, which was statistically significant (day3; p=0.035, day4; p=0.00007). QR2 shRNA injected mice were significantly more efficient on the latency to find the platform on fourth day of the acquisition phase compared to scrambled virus injected animals (t18=-2.267,p=0.036 paired t-test). FIG. 14B shows that after completion of training, QR2 shRNA injected mice showed preferential quadrant occupancy in comparison with scrambled injected mice (t18=-2.345, p=0.031 paired t-test). FIG. 14C shows that QR2 shRNA injected mice crossed the site where the platform was located more times (t18=-2.373, p=0.029 paired t-test) than scrambled injected mice. All results are means±SEM FIG. 15A shows that the animals which were injected with one of the QR2 inhibitors formed better memories of the taste during the pre-exposure period, as evident from the lower aversion index (AI). The group which was exposed to the novel taste once before being subjected to the CTA protocol (LI-CTA (Veh)) had a significantly lower AI than the group which was subjected only to the CTA protocol (CTA (Veh) one-way ANOVA with Fisher's Least Significant Difference post-hoc test, n=8, *p<0.05). The group which was injected with S29434 before undergoing the LI-CTA protocol (LI-CTA (S29434)) had a significantly lower AI than both the group which only underwent CTA (p<0.001) and the group which was injected with the vehicle before undergoing the LI-CTA protocol (p<0.001). The group injected with S26695 (LI-CTA (S26695)) before undergoing the LI-CTA protocol had a significantly lower AI than both the group which only underwent CTA (**p<0.001) and the group which was injected with the vehicle before undergoing the LI-CTA protocol (*p<0.05). There was no significant difference in the AI between the group injected with S29434 and the group injected with S26695 (one-way ANOVA with Fisher's Least Significant Difference post-hoc test, n=8, P>0.05). FIG. 15B shows that the inventors of the present application determined that the injection of the vehicle or the inhibitors did not affect the extinction (repeated measures ANOVA with Greenhouse-Geisser correction, n=8, # p<0.001).

FIG. 16A shows that animals injected with the QR2 inhibitors formed stronger memories of the taste as can be seen from their higher AI. Animals injected with S29434 or S26695 had a significantly higher AI than those injected with the vehicle (one-way ANOVA with Fisher's Least Significant Difference Test, n=8, **p<0.005 or *p<0.01, respectively). There was no significant difference in the AI between the group injected with S29434 and the group injected with S26695 (p>0.05). FIG. 16B shows that the inventors of the present application determined that the injection of the vehicle or the inhibitors did not affect memory extinction (repeated measures ANOVA with Greenhouse-Geisser correction, n=8, # p<0.001).

FIG. 17A shows that QR2 mRNA expression is significantly higher in AD patients compared to healthy controls (unpaired Student's t-test, AD patients: n=28, Heathy controls: n=1, *p<0.05). FIG. 17B shows that QR2 mRNA relative quantities are correlated with Aβ40 levels, (Pearson correlation coefficient test, n=38 (11 healthy controls, 27 AD patients), R=0.56, p value=0.0002.

DETAILED DESCRIPTION OF THE PREFERRED EMBODIMENT

Figure 1:
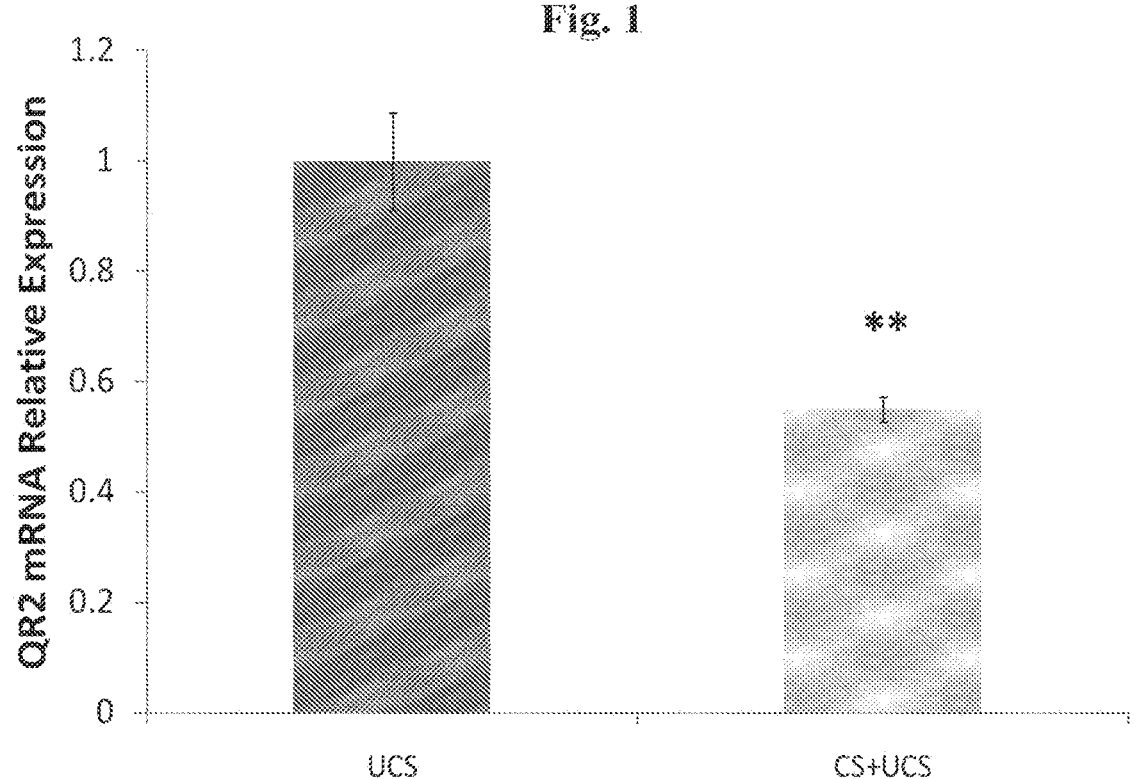
FIG. 1 shows that associative taste learning leads to a significant reduction in quinone reductase 2 (QR2) mRNA expression in the insular cortex (IC) compared to the control, which did not undergo a taste learning paradigm. The RT-PCR results are expressed here and after as relative QR2 mRNA expression with QR2 being normalized to GAPDH. The pairing of the saccharin (conditioned stimulus (CS)) with the malaise inducing LiCl injection (unconditioned stimulus (UCS)) causes about 45% reduction in QR2 mRNA expression in the insular cortex when compared to the control group which was only exposed to the UCS (unpaired Student's t-test, n=10, **$p<0.005$; error bars represent standard error of the mean (SEM)).

Quinones are a class of naturally occurring compounds which are present in organic foods, cigarette smoke, and car exhaust among other organic compounds. They are highly reactive compounds which can go through either a two-electron reduction rendering them relatively harmless or a one-electron reduction leading to the creation of reactive oxygen species (ROS) which are extremely reactive and can have many deleterious effects on the organism.

In mammals there are two primary quinone reductases: quinone reductase 1 (QR1) and quinone reductase 2 (QR2). The human gene for QR2 is located on chromosome 6p25 and is 20 kBP in length (Jaiswal, 1994). It encodes a homodimer with each monomer being 231 amino acids (AA) (Vella et al., 2005). QR2 is highly conserved and is 81% homologous between humans and rats (BLAST) and 82% homologous between humans and mice (Long et al., 2000). Immunostaining shows that QR2 distribution in the brain is similar in both rodents and humans. QR2 staining is particularly abundant in regions associated with cognition such as the hippocampus and a variety of cortical areas. Additionally, QR2 appears to be localized in the cytoplasm of neurons (Benoit et al., 2010).

The QR2 enzyme catalyzes an electron reduction in quinones. Currently very little is known about the natural substrates and co-substrates of QR2. Unlike QR1 activity, which always leads to quinones being less reactive, QR2 enzymatic activity sometimes leads to quinones being more reactive resulting in more reactive oxygen species (ROS) in the cell and sometimes leads to quinones being less reactive. Therefore, in certain cases, QR2 activity as opposed to QR1 activity leads to cell toxicity (Vella et al., 2005). From the literature it appears that QR2 primarily leads to decreased ROS in non-neuronal cells and to increased ROS in neurons.

Inhibitors of QR2 Activity—

Melatonin is known to have three binding sites in the brain, one of which has been shown to be QR2 (Mailliet et al., 2004) where it binds to the QR2 catalytic site and inhibits QR2 activity. This may explain the known antioxidant properties of melatonin (Mailliet et al., 2005). Another compound which has known health benefits and antioxidant properties is resveratrol, a compound found in red wine and believed to be behind the so called "French paradox". It has since been found that resveratrol targets (Wang Z et al., 2004) and efficiently inhibits QR2 (Buryanovskyy et al., 2004). In addition to these natural inhibitors of QR2 enzymatic activity there are numerous synthetic inhibitors, which bind to the QR2 catalytic binding site and which, while similar in structure, are more potent and stable than both melatonin and resveratrol (Ferry et al., 2010).

QR2 and Diseases—

The majority of the research relating to QR2 and associated diseases has been focused on its role in skin cancer and malaria. It has been found that mice, which had the QR2 gene knocked out, are more susceptible to skin cancer. The theory is that this is due to the increased ROS in the cells which disrupts the cell's protective mechanisms (Iskander et al., 2004).

The search for the molecular targets of anti-malaria drugs led to QR2 (Graves et al., 2002). It is well known that increased ROS can have beneficial effects in organisms infected with malaria since it prevents further infection by the parasite. The anti-malaria drugs lead to increased ROS through the inhibition of QR2. Uninhibited QR2 normally leads to less ROS in cells but when inhibited by the anti-malaria drugs are unable to stabilize quinones, leading to increased ROS, to which the parasite is sensitive. This increase in ROS protects against the malaria parasite (Kwiek et al., 2004).

QR2 and Neurological Diseases—

QR2 expression is correlated with neurological diseases. Schizophrenic patients overexpress QR2 in comparison to healthy subjects due to a mutation in the promoter region for the QR2 gene (Harada et al., 2003; Wang et al., 2004). This same phenomenon has been noted in patients with Parkinson's disease (Harada et al., 2001; Wang et al., 2004) and Alzheimer's disease (Hashimoto et al., 2011). Aged rats which were shown to be impaired cognitively had higher levels of QR2 expression as opposed to aged rats which were unimpaired cognitively. Additionally, rats which were subjected to scopolamine, a muscarinic acetylcholine receptor (mAChR) antagonist, which is used to induce animal models of neurodegenerative diseases, also overexpressed QR2 (Brouillette and Quirion, 2008). The exact mechanism by which the overexpression of QR2 is involved with these disorders is unknown but theorized to be related to damage due to ROS.

Quinone Reductase 2 (QR2) has recently been shown to play a role in learning and memory. Mice in which the QR2 gene has been knocked out (KO) show improved learning in hippocampal-dependent tasks. The QR2 KO mice showed improved spatial learning and memory as well as enhanced object recognition (Benoit et al., 2010). These results indicate that QR2 plays a negative role in the learning process.

Cognition is a complex process involving among others memory and learning. Taste learning, like other forms of learning, requires the regulation of both transcription and translation (e.g. Bailey et al., 1996; Meiri et al., 1998, and Rosenblum, 1998). It has been found in accordance with the present invention that novel taste learning results in reduction in QR2 mRNA expression (Examples 1-4, 6 and 7) and conversely that a decrease in the level of expression (Examples 9 to 11) or activity (Examples 14 and 15) of quinone reductase 2 results in enhanced taste learning. However, as it can be clearly seen from Examples 12 and 13, the effect of reduction of QR2 level is not limited to taste learning only, but it is related to more general learning abilities involving different brain regions such as the IC and hippocampus. It can further be seen from the temporal dynamics of QR2 mRNA expression during the consolidation period that QR2 mRNA expression is reduced when long-term memory is formed (Example 5 and 12-13) and that reducing the QR2 mRNA expression by means of shRNA results in significant memory extinction on day 3 after learning. These findings suggest that inhibition of QR2 mRNA expression improves both memory consolidation and extinction and thus plasticity (Example 10).

In view of the above, in one aspect, the present invention provides an active agent capable of reducing quinone reductase 2 activity, for use in improvement of cognition in a subject.

The terms "cognition", "cognitive function" and "cognitive performance" are used herein interchangeably and are related to any mental process or state that involves but is not limited to learning, memory, creation of imagery, thinking, awareness, reasoning, spatial ability, speech and language skills, language acquisition and capacity for judgment attention. Cognition is formed in multiple areas of the brain such as hippocampus, cortex and other brain structures. It is assumed that long term memories are stored at least in part in the cortex and it is known that sensory information is acquired, consolidated and retrieved by a specific cortical structure, the gustatory cortex, which resides within the insular cortex. Another region that has been shown to be responsible for memory formation and long term storage is hippocampus.

In humans, cognitive function may be measured by any known method, for example and without limitation, by the clinical global impression of change scale (CIBIC-plus scale); the Mini Mental State Exam (MMSE); the Neuropsychiatric Inventory (NPI); the Clinical Dementia Rating Scale (CDR); the Cambridge Neuropsychological Test Automated Battery (CANTAB) or the Sandoz Clinical Assessment-Geriatric (SCAG). Cognitive function may also be measured indirectly using imaging techniques such as Positron Emission Tomography (PET), functional magnetic resonance imaging (fMRI), Single Photon Emission Computed Tomography (SPECT), or any other imaging technique that allows one to measure brain function.

An improvement of one or more of the processes affecting the cognition in a patient will signify an improvement of the cognitive function in said patient, thus in certain embodiments improving cognition comprises improving learning, plasticity, and/or long term memory. The terms "improving" and "enhancing" may be used interchangeably.

The term "learning" relates to acquiring or gaining new, or modifying and reinforcing existing knowledge, behaviors, skills, values, or preferences.

The term "plasticity" relates to synaptic plasticity, brain plasticity or neuroplasticity associated with the ability of the brain to change with learning, and to change the already acquired memory. One measurable parameter reflecting plasticity is memory extinction.

The term "memory" relates to the process in which information is encoded, stored, and retrieved. Memory has three distinguishable categories: sensory memory, short-term memory, and long-term memory.

The term "long term memory" is the ability to keep information for a long or unlimited period of time. Long term memory comprises two major divisions: explicit memory (declarative memory) and implicit memory (non-declarative memory). Long term memory is achieved by memory consolidation which is a category of processes that stabilize a memory trace after its initial acquisition. Consolidation is distinguished into two specific processes: synaptic consolidation, which occurs within the first few hours after learning, and system consolidation, where hippocampus-dependent memories become independent of the hippocampus over a period of weeks to years.

An improvement of one or more of explicit memory, implicit memory, memory consolidation, synaptic consolidation or system consolidation will signify an improvement of long-term memory.

The term "patient", "subject", or "individual" are used interchangeably and refer to either a human or a non-human animal.

It has been found in accordance with the present invention that reducing the expression level of QR2 by the means of siRNA molecules specific for the QR2 gene results in improved cognition in the treated subject (Examples 9 to 13). According to the present invention, an active agent capable of reducing the expression level of quinone reductase 2 may be any molecule that may inhibit or reduce the expression of QR2. Non-limiting examples of such molecules are small interfering RNA molecules (siRNA), small hairpin RNA molecules (shRNA), oligodeoxynucleotides or peptide nucleic acids. Thus, in one embodiment the active agent capable of reducing quinone reductase 2 activity is a nucleic acid molecule that reduces the gene expression level of quinone reductase 2. In some embodiments, QR2 expression is reduced but not completely eliminated.

Small interfering RNA molecules are short double stranded RNA molecules capable of reducing the expression level of a protein by inhibiting, reducing or eliminating gene expression through degradation of the target mRNA (in case of perfect match) or inhibition of mRNA translation (in case of imperfect match). The siRNA molecules may be artificial siRNA.

The term "shRNA" refers to an artificial double-stranded small hairpin RNA having a stem-loop structure and comprising 19-29 nucleotide. The shRNA is capable of reducing the expression level of a protein by inhibiting, reducing or eliminating gene expression through degradation of the target mRNA (in case of perfect match) or inhibition of mRNA translation (in case of imperfect match).

This nucleic acid molecule capable of reducing the expression level of quinone reductase 2 according to the present invention may therefore be an artificial and/or isolated siRNA or shRNA molecule comprising a nucleic acid sequence being complementary to a sequence within a nucleic acid sequence encoding the quinone reductase 2, or a nucleic acid molecule encoding such an artificial siRNA or shRNA molecule. In some embodiments, the isolated/artificial siRNA or shRNA molecule comprises a nucleic acid sequence having a sequence identity of 90% or more, e.g. 95% or more, 98% or more, or 99% identity to the quinone reductase 2. In another embodiment the siRNA or shRNA molecule comprises a nucleic acid sequence being perfectly complementary to a sequence within the sequence encoding of quinone reductase 2. In certain embodiments the siRNA or shRNA molecule comprises a sequence corresponding to SEQ ID NO: 5, 6 or 7.

The quinone reductase 2 according to the present invention may be mammalian quinone reductase 2. In certain embodiments the quinone reductase 2 is a human quinone reductase 2 encoded by a nucleic acid sequence herein identified as SEQ ID NO: 1. In another embodiment the siRNA or shRNA molecule comprises a sequence corresponding to SEQ ID NO: 2, 3 or 4.

The ability of an active agent to reduce expression of quinone reductase 2 (QR2) may be tested by a person skilled in the art by using any known method, e.g. using as a model any cell line expressing QR2 or primary cortical cells, as described in the Material and Method part. The quantification of the QR2 gene expression level in these cells may be done by any known method, e.g. by real time PCR as described in the Material and Methods part.

Having demonstrated that genetically decreasing QR2 expression in the IC and hippocampus enhances learning, we hypothesized that pharmacologically inhibiting QR2 activity would have a similar effect. We evaluated this hypothesis through the use of two different QR2 inhibitors. Our results prove that inhibiting QR2 activity enhances positive (Example 14) as well as negative (Example 15) taste learning.

Thus, the invention also provides an active agent capable of inhibiting quinone reductase 2 activity for use in improvement of cognition in a subject who is not treated with scopolamine. In other words, the invention provides an inhibitor of quinone reductase 2 activity for use in improvement of cognition. The active agent, according to some embodiments, may inhibit quinone reductase 2 activity of a mammalian quinone reductase 2, thus being a quinone reductase 2 inhibitor. In a more particular embodiment the quinone reductase 2 is a human quinone reductase 2 (hQR2), thus the active agent is a human quinone reductase 2 inhibitor.

The assessment of the inhibition potency of the active agent may be done by any method known in the art, e.g. by in vitro measurement of QR2 enzymatic activity in the presence of the active agent and identification of its inhibition constant ($k_i$), as described below in the M&M section.

The active agent reducing the hQR2 activity may be a small molecule capable of inhibiting, reducing or eliminating the activity of hQR2. For example, the active agent may be an hQR2 reversible or irreversible inhibitor, and the reversible inhibitor may be competitive, non-competitive or uncompetitive. Therefore, according to one embodiment, the hQR2 inhibitor is a competitive inhibitor. Non-limiting examples of QR2 inhibitors that may be used in accordance with the present invention comprise N-[2-(2-methoxy-6h-dipyrido[2,3-α:3,2-e]pyrrolizin-11-yl)ethyl]-2-furamide, herein identified as S29434; N-[2-(7-methylaminosulfonyl-1-naphthyl)ethyl]acetamide, herein identified as S26695; 2-hydroxy-8,9-dimethoxy-6h-isoindolo[2,1-a]indol-6-one, herein identified as S32797; 1-benzyl-1,4-dihydronicotinamide; 1-(β-d-ribofuranosyl)-1,4-dihydronicotinamide; 2,6-dichlorophenol indophenol; methyl-1-(2-acetamidoethyl)-7-naphthylcarbamate; N-[2-(5-methoxy-4-nitro-1h-indol-3-yl)ethyl]acetamide; N-[2-(5-methoxy-7-nitro-1h-indol-3-yl)ethyl]acetamide; N-[2-(2-iodo-5-methoxy-1-methyl-4-nitroindol-3-yl)ethyl]acetamide; 2-iodo-N-[2-(2-methoxy-6hpyrido[2',3':4,5]pyrrolo[2,1-a]isoindol-11-yl)ethyl]-benzamide; 2-iodo-melatonine; chrysoeriol; resveratrol; menadione; melatonine; coenzyme Q2; N-[2-(8-methoxy-3,4-dihydro-2h-pyrido[2',3':4,5]pyrrolo[2,1-b][1,3]oxazin-10-yl)ethyl]-2-furamide; N1-[2-(2-methoxy-6h-pyrido[2',3':4,5]pyrrolo[2,1-a]isoindol-11-yl)ethyl]-acetamide; N-[2-(2-methoxy-6h-pyrido[2',3':4,5]-pyrrolo[2,1-a]isoindol-11-yl)ethyl]-2-furamide; 2-(2-methoxy-6h-pyrido[2',3':4,5]pyrrolo[2,1-a]isoindol-11-yl)ethylamine(1,6) oxalate; or methyl (3-(2-acetamidoethyl)-2-iodo-1h-indol-5-yl)carbamate or pharmaceutically acceptable salts thereof. The structures of the aforementioned inhibitors are provided in Table 1. In certain embodiments, the hQR2 inhibitor is a competitive inhibitor, in particular S26695, S32797 or S29434, or pharmaceutically acceptable salts thereof. According to the present invention, any pharmaceutically acceptable salt of the active agent can be used. Examples of pharmaceutically acceptable salts include, without being limited to, the mesylate salt, the esylate salt, the tosylate salt, the sulfate salt, the sulfonate salt, the phosphate salt, the carboxylate salt, the maleate salt, the fumarate salt, the tartrate salt, the benzoate salt, the acetate salt, the hydrochloride salt, and the hydrobromide salt.

S26695 and S29434 (CAS: 874484-20-5) may be prepared by any known method; e.g. S26695 may be prepared as described in WO 99058496.

TABLE 1

QR2 INHIBITORS

| Compound Name | Structure | Compound Name | Structure |
| --- | --- | --- | --- |
| N-[2-(2-methoxy-6H-dipyrido[2,3-α:3,2-e]pyrrolizin-11-yl)ethyl]-2-furamide (S29434) | 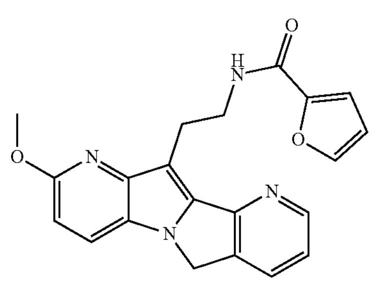 [SMILES: COc1ccc2c(n1)c(CCNC(=O)c1ccco1)c1n2Cc2cccnc2-1] | Chrysoeriol | 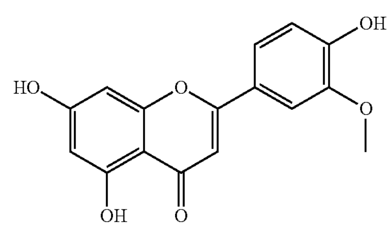 [SMILES: COc1cc(-c2cc(=O)c3c(O)cc(O)cc3o2)ccc1O] |
| N-[2-(7-methylaminosulfonyl-1-naphthyl)ethyl]acetamide (S26695) | 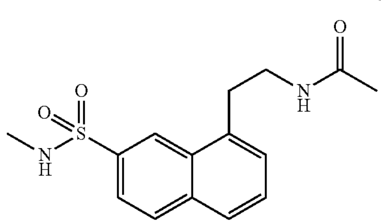 | Resveratrol | 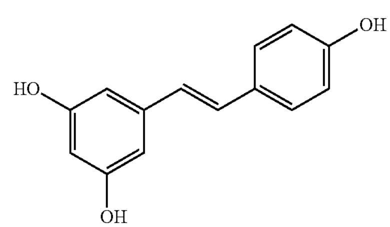 [SMILES: Oc1ccc(/C=C/c2cc(O)cc(O)c2)cc1] |

TABLE 1-continued

QR2 INHIBITORS

| Compound Name | Structure | Compound Name | Structure |
| --- | --- | --- | --- |
| 1-benzyl-1,4-dihydronicotinamide (BNAH) | 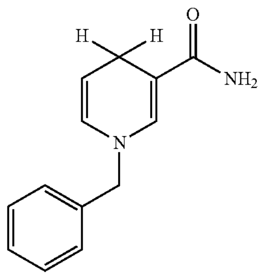 [SMILES: NC(=O)C1=CN(Cc2ccccc2)C=CC1] | Menadione | 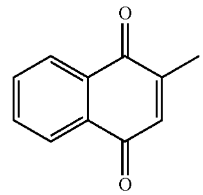 |
| 1-(β-d-ribofuranosyl)-1,4-dihydronicotinamide (NRH) | 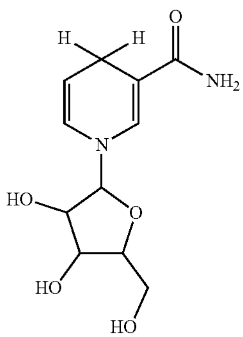 | Melatonine | 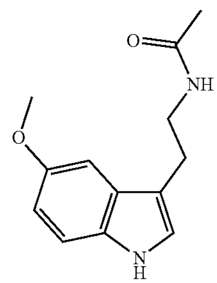 [SMILES: COc1ccc2[nH]cc(CCNC(C)=O)c2c1] |
| 2,6-dichlorophenol indophenol (DCPIP) | 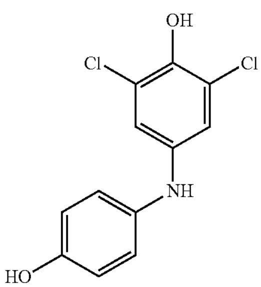 [SMILES: Oc1ccc(Nc2cc(Cl)c(O)c(Cl)c2)cc1] | Coenzyme Q2 | 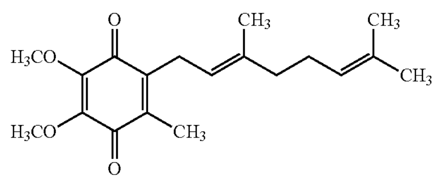 [SMILES: COC1=C(OC)C(=O)C(C/C=C(\C)CCC=C(C)C)=C(C)C1=O] |
| methyl-1-(2-acetamidoethyl)-7-naphthylcarbamate | 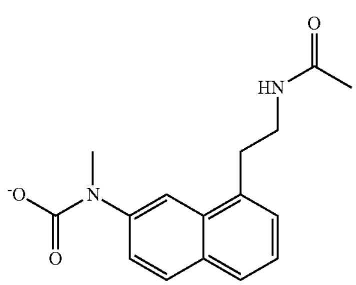 | N-[2-(8-methoxy-3,4-dihydro-2H-pyrido[2',3':4,5]pyrrolo[2,1-b][1,3]oxazin-10-yl)ethyl]-2-furamide | 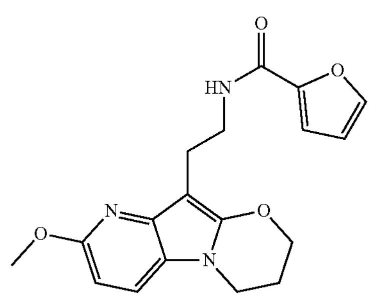 [SMILES: COc1ccc2c(n1)c(CCNC(=O)c1ccco1)c1n2CCCO1] |
| N-[2-(5-methoxy-4-nitro-1H-indol-3-yl)ethyl]acetamide | 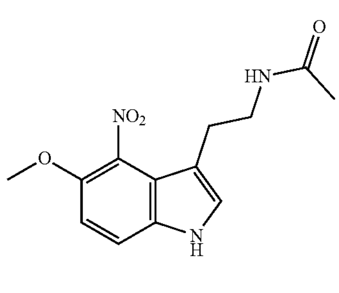 [SMILES: COc1ccc2[nH]cc(CCNC(C)=O)c2c1[N+](=O)[O-]] | N1-[2-(2-methoxy-6H-pyrido[2',3':4,5]pyrrolo[2,1-a]isoindol-11-yl)ethyl]-acetamide | 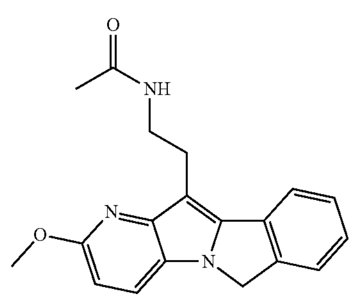 [SMILES: COc1ccc2c(n1)c(CCNC(C)=O)c1n2Cc2ccccc2-1] |

TABLE 1-continued

QR2 INHIBITORS

| Compound Name | Structure | Compound Name | Structure |
| --- | --- | --- | --- |
| N-[2-(5-methoxy-7-nitro-1H-indol-3-yl)ethyl]acetamide | 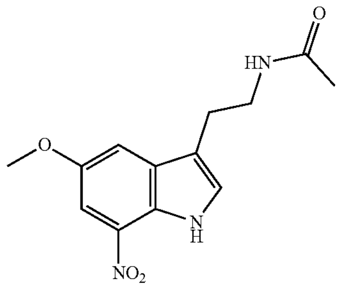 [SMILES: COc1cc([N+](=O)[O-])c2[nH]cc(CCNC(C)=O)c2c1] | N-[2-(2-methoxy-6H-pyrido[2',3':4,5]-pyrrolo[2,1-a]isoindol-11-yl)ethyl]-2-furamide | 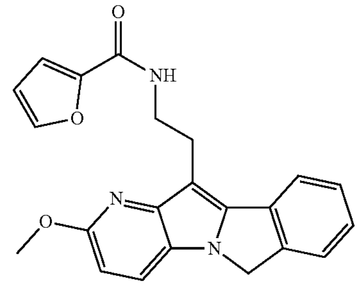 [SMILES: COc1ccc2c(n1)c(CCNC(=O)c1ccco1)c1n2Cc2ccccc2-1] |
| N-[2-(2-iodo-5-methoxy-1-methyl-4-nitroindol-3-yl)ethyl]acetamide | 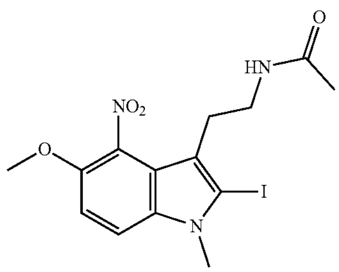 [SMILES: COc1ccc2c(c(CCNC(C)=O)c(I)n2C)c1[N+](=O)[O-]] | 2-(2-methoxy-6H-pyrido[2',3':4,5]pyrrolo[2,1-a]isoindol-11-yl)ethylamine(1,6) oxalate | 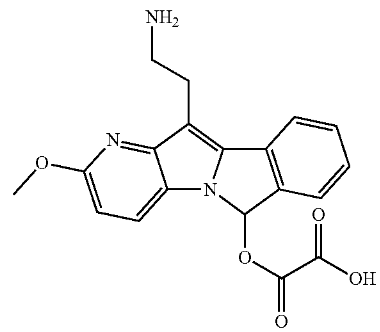 [SMILES: COc1ccc2c(n1)c(CCN)c1n2C(OC(=O)C(=O)O)c2ccccc2-1] |
| 2-iodo-N-[2-(2-methoxy-6Hpyrido[2',3':4,5]pyrrolo[2,1-a]isoindol-11-yl)ethyl]-benzamide | 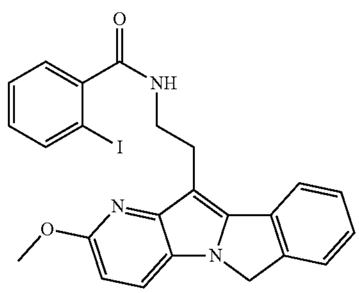 [SMILES: COc1ccc2c(n1)c(CCNC(=O)c1ccccc1I)c1n2Cc2ccccc2-1] | methyl (3-(2-acetamidoethyl)-2-iodo-1H-indol-5-yl)carbamate (2-I-MCA-NAT) | 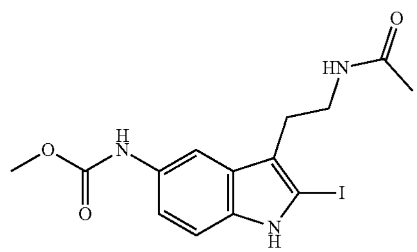 [SMILES: COC(=O)Nc1ccc2[nH]c(I)c(CCNC(C)=O)c2c1] |
| 2-iodo-melatonine | 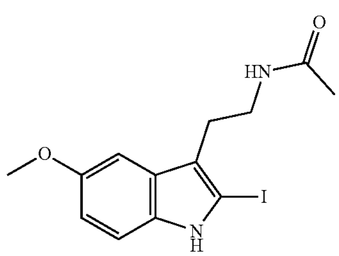 [SMILES: COc1ccc2[nH]c(I)c(CCNC(C)=O)c2c1] | 2-hydroxy-8,9-dimethoxy-6H-isoindolo[2,1-a]indol-6-one (S32797) | 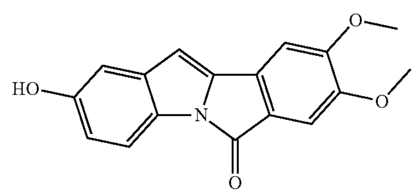 [SMILES: COc1cc2c(cc1OC)-c1cc3cc(O)ccc3n1C2=O] |

The terms "reduces", "reducing" and "causes reduction" may be used interchangeably herein and contemplate direct reduction of quinone reductase 2 activity or indirect reduction of same. Direct reduction may be a direct impact or effect of an active agent on the level of QR2 activity by directly reducing the level of QR2 expression or the level of QR2 enzymatic activity. In other words, the active agent directly interacts with and inhibits QR2 enzymatic activity or transcription or translation of a QR2 encoding gene. The indirect reduction is not caused by the active agent itself, but by a secondary molecule generated or derived from the active agent, such as a molecule encoded by the active agent. One example would be a nucleic acid molecule that by itself does not affect QR2 expression, but which encodes an shRNA that does decrease QR2 expression.

In certain embodiments, the improvement of cognition comprises improvement of learning, plasticity and/or long term memory, each as defined above. In certain embodiments, the cognition as defined above may be an insular cortex dependent cognition and/or hippocampus dependent cognition.

The term "insular cortex" as used herein refers to a portion of the cerebral cortex folded deep within the lateral sulcus of each of the hemispheres of the brain. The term may be used interchangeably with terms "insula", "insulary cortex" or "insular lobe". The anterior portion of the insular cortex comprises the primary cortical taste area that is associated with several functions, among which are taste perception, learning and memory abilities. In addition it is associated with auditory and pain recognition and processing and memory, e.g. recognition memory.

The term "hippocampus" or "hippocampal" refers to a portion in the brain located in the medial temporal lobe, underneath the cortical surface. Its structure is divided into two halves which lie in the left and right sides of the brain. The hippocampus has a curved shape that resembles a seahorse. It belongs to the limbic system and plays important roles in the system consolidation of information from short-term memory to long-term memory and spatial navigation. The hippocampus plays an important role in the formation of new memories about experienced events and in the detection of novel events, places and stimuli as well as in forming general declarative memory (memories that can be explicitly verbalized).

In certain embodiments the subject as defined above may be a healthy, normal subject having normal cognitive function or a subject suffering from a disease, disorder, condition or injury characterized by cognitive impairment. In one particular embodiment the subject is a healthy subject and the term "healthy" relates to a person not suffering from a cognitive impairment.

Example 16 shows that subjects suffering from Alzheimer's disease express chronically higher levels of QR2 mRNA in the frontal cortex. Thus in certain embodiments, the subject is a subject suffering from a disease, disorder, condition or injury characterized by cognitive impairment, such as, but not limited to Alzheimer's disease, Parkinson's disease, amnesia such as electric shock induced amnesia, dementia such as multi-infarct dementia or senile dementia, amyotrophic lateral sclerosis, a brain injury, cerebral senility, chronic peripheral neuropathy, cognitive disability, degenerative disorder associated with a learning and memory deficit, defective synaptic transmission, Down's syndrome, dyslexia, Guillain-Barre syndrome, head trauma, stroke, cerebral ischemia, Huntington's disease, a learning disability, a memory deficiency, memory loss, a mental illness, mental retardation, memory or cognitive dysfunction, myasthenia gravis, a neuromuscular disorder, Pick's disease, a reduction in spatial memory retention, senility, Tourette's syndrome, cardiac arrest, open heart surgery, chronic fatigue syndrome, epileptic seizures, major depression or electroconvulsive therapy. In particular, the subject is one suffering from Alzheimer's disease, Parkinson's disease, amnesia or dementia.

The term "cognitive impairment" refers to a condition in which a subject does not have cognition as robust as that expected in an age-matched population of normal subjects.

In another aspect the present application provides a vector comprising an active agent that reduces the gene expression level of quinone reductase 2 as defined hereinabove.

The term "vector" refers to any viral or non-viral vector, as well as any plasmid, cosmid, phage or binary vector in double or single stranded linear or circular form that may or may not be self-transmissible or mobilizable, and that can transform eukaryotic host cells either by integration into the cellular genome or which can exist extrachromosomally (e.g., autonomous replicating plasmid with an origin of replication). Any vector known in the art is envisioned for use in the practice of this invention.

The vector according to the invention is used for transferring a nucleic acid (or nucleic acids), such as shRNA, siRNA or a construct encoding shRNA or siRNA, to a host cell; it optionally comprises a viral capsid or other materials for facilitating entry of the nucleic acid into the host cell and/or replication of the vector in the host cell.

The vector of the present invention may be a modified or engineered virus. The modification of a vector may include mutations, such as deletion or insertion mutation, gene deletion or gene inclusion. In particular, a mutation may be done in one or more regions of the viral genome. Such mutations may be introduced in a region related to internal structural proteins, replication, or reverse transcription function. Other examples of vector modification are deletion of certain genes constituting the native infectious vector such as genes related to the virus' pathogenicity and/or to its ability to replicate. The modification of the vectors may be done by any known method e.g. as described in U.S. Pat. Nos. 7,749,973, 6,610,287 or US 2013/0287736, expressly incorporated herein in their entireties by reference.

Thus in one embodiment the vector (e.g. viral vector) according to the present invention comprises a nucleic acid molecule encoding an artificial siRNA or shRNA molecule comprising a nucleic acid sequence being complementary to a sequence within a nucleic acid sequence encoding the quinone reductase 2. In some embodiments the nucleic acid molecule encodes an siRNA or shRNA molecule comprising a nucleic acid sequence having a sequence identity of 90% or more, e.g. 95% or more, 98% or more, or 99% or more identity to the quinone reductase 2. In another embodiment, the nucleic acid molecule encodes an siRNA or shRNA molecule comprising a nucleic acid sequence being perfectly complementary to the sequence of quinone reductase 2. In still another embodiment the vector comprises a nucleic acid molecule encoding an siRNA or shRNA molecule comprising a sequence corresponding to SEQ ID NO: 5, 6 or 7. In certain embodiments, the nucleic acid molecule encodes an siRNA or shRNA molecule comprising a nucleic acid sequence complementary to the sequence of a human quinone reductase 2. Such artificial siRNA or shRNA may comprise a nucleic acid sequence having a sequence identity of 90% or more, e.g. 95% or more, 98% or more, or 99% or more identity to a human quinone reductase 2. In another embodiment the vector comprises a nucleic acid molecule encoding an artificial siRNA or shRNA molecule comprising a nucleic acid sequence being perfectly complementary to the sequence of a human quinone reductase 2. In still another embodiment the vector comprises a nucleic acid molecule encoding an siRNA or shRNA molecule comprising a sequence corresponding to SEQ ID NO: 2, 3 or 4. Even though SEQ ID NOs: 2-7 denote RNA sequences, it should be understood that DNA molecules encoding an artificial siRNA or shRNA molecule identified by these SEQ ID NOs have corresponding DNA sequences (i.e. U is replaced with T).

In certain embodiments the vector is a modified virus derived from a virus. A non-limiting example of viruses from which the vector may be constructed comprises retrovirus, adenovirus, adeno-associated virus, pox virus, alphavirus, herpes virus, or lentivirus. In particular, the vector may be is a modified lentivirus. Thus in certain embodiments the vector is a modified lentivirus comprising a nucleic acid molecule encoding an shRNA molecule comprising a sequence being complementary to a sequence within a nucleic acid sequence encoding human quinone reductase 2. Such a modified lentivirus encoding the shRNA molecule may be obtained by any method known in the art. For example a nucleic acid molecule encoding an shRNA operably linked to a promoter may be subcloned into a lentiviral (LV) plasmid for expression of the shRNA driven by the promoter, optionally coexpressed with EGFP under control of another promoter. Such cassettes containing the shRNA sequences, EGFP, and the promoters may be cotransfected into a cell line, such as 293FT, and allowed to express and form viral particles. The viral particles may be then collected and used.

A non-viral vector, according to the present invention may be, without being limited to, lipids, such as cationic lipids and in particular liposomes; amphiphilic copolymers; polycationic nanocarriers such as polyethyleneimine and chitosan; highly branched macromolecules, also known as dendrimers, forming e.g. spherical shapes; or cyclodextrin. Such compounds may encapsulate the nucleic acid molecule of the invention or form complexes with it.

In still another aspect the present invention provides a pharmaceutical composition comprising an active agent or a vector, according to any one of the above embodiment and a pharmaceutically acceptable carrier. In one embodiment the pharmaceutical composition comprises a pharmaceutically acceptable carrier and an active agent capable of reducing quinone reductase 2 activity. Such a pharmaceutical composition may comprise a nucleic acid molecule that reduces the gene expression level of quinone reductase 2 or a nucleic acid molecule encoding a nucleic acid that reduces the gene expression level of quinone reductase 2. In some embodiments the pharmaceutical composition comprises a pharmaceutically acceptable carrier and an artificial and/or isolated siRNA or shRNA molecule comprising a nucleic acid sequence being complementary to a sequence within a nucleic acid sequence encoding said quinone reductase 2, more particularly siRNA or shRNA comprising a nucleic acid sequence molecule having a sequence identity of 90% or more, e.g. 95% or more, 98% or more, or 99% or more identity to the quinone reductase 2 or being perfectly complementary to the sequence of quinone reductase 2, e.g. comprising a sequence corresponding to SEQ ID NO: 5, 6 or 7. In another embodiment the pharmaceutical composition comprises a pharmaceutically acceptable carrier and the artificial siRNA or shRNA molecule comprising a nucleic acid sequence complementary to the sequence of a human quinone reductase 2, particularly siRNA or shRNA comprising a nucleic acid sequence having a sequence identity of 90% or more, e.g. 95% or more, 98% or more, or 99% or more identity to a human quinone reductase 2 and more particularly a siRNA or shRNA molecule comprising a nucleic acid sequence being perfectly complementary to the sequence of a human quinone reductase 2, e.g. comprising a sequence corresponding to SEQ ID NO: 2, 3 or 4. In another embodiment, the pharmaceutical composition comprises a pharmaceutically acceptable carrier and a vector comprising and/or encoding any one of the aforementioned siRNA or shRNA molecules.

In still another embodiment the pharmaceutical composition comprises a pharmaceutically acceptable carrier and active agent capable of inhibiting quinone reductase 2 activity, such as small molecules inhibitors of QR2. In particular embodiment the pharmaceutical composition comprises a pharmaceutically acceptable carrier and an active agent inhibiting quinone reductase 2 activity of a mammalian quinone reductase 2, more particular of a human quinone reductase 2 (hQR2). In more particular embodiment the pharmaceutical composition comprises N-[2-(2-methoxy-6h-dipyrido[2,3-α:3,2-e]pyrrolizin-11-yl)ethyl]-2-furamide, herein identified as S29434; N-[2-(7-methylaminosulfonyl-1-naphthyl)ethyl]acetamide, herein identified as S26695; 2-hydroxy-8,9-dimethoxy-6h-isoindolo[2,1-a]indol-6-one, herein identified as S32797; 1-benzyl-1,4-dihydronicotinamide; 1-(β-d-ribofuranosyl)-1,4-dihydronicotinamide; 2,6-dichlorophenol indophenol; methyl-1-(2-acetamidoethyl)-7-naphthylcarbamate; N-[2-(5-methoxy-4-nitro-1h-indol-3-yl)ethyl]acetamide; N-[2-(5-methoxy-7-nitro-1h-indol-3-yl)ethyl]acetamide; N-[2-(2-iodo-5-methoxy-1-methyl-4-nitroindol-3-yl)ethyl]acetamide; 2-iodo-N-[2-(2-methoxy-6hpyrido[2',3':4,5]pyrrolo[2,1-a]isoindol-11-yl)ethyl]-benzamide; 2-iodo-melatonine; chrysoeriol; resveratrol; menadione; melatonine; coenzyme Q2; N-[2-(8-methoxy-3,4-dihydro-2h-pyrido[2',3':4,5]pyrrolo[2,1-b][1,3]oxazin-10-yl)ethyl]-2-furamide; N1-[2-(2-methoxy-6h-pyrido[2',3':4,5]pyrrolo[2,1-a]isoindol-11-yl)ethyl]-acetamide; N-[2-(2-methoxy-6h-pyrido[2',3':4,5]-pyrrolo[2,1-a]isoindol-11-yl)ethyl]-2-furamide; 2-(2-methoxy-6h-pyrido[2',3':4,5]pyrrolo[2,1-a]isoindol-11-yl) ethylamine(1,6) oxalate; or methyl (3-(2-acetamidoethyl)-2-iodo-1h-indol-5-yl)carbamate, or a pharmaceutically acceptable salt thereof.

The vector or pharmaceutical composition of the present invention may be used for improvement of cognition in a subject. In case of the QR2 inhibitor, the subject is not treated with scopolamine.

Pharmaceutical compositions in accordance with the present invention may be formulated in conventional manner using one or more physiologically acceptable carriers and/or excipients. The carrier(s) must be "acceptable" in the sense of being compatible with the other ingredients of the composition and not deleterious to the recipient thereof.

The following exemplification of carriers, modes of administration, dosage forms, etc., are listed as known possibilities from which the carriers, modes of administration, dosage forms, etc., may be selected for use with the present invention. Those of ordinary skill in the art will understand, however, that any given formulation and mode of administration selected should first be tested to determine that it achieves the desired results.

Methods of administration include, but are not limited to, parenteral, e.g., intravenous, intraperitoneal, intramuscular, subcutaneous, mucosal (e.g., oral, intranasal, buccal, vaginal, rectal, intraocular), intrathecal, topical and intradermal routes. Administration can be systemic or local. In certain embodiments, the pharmaceutical composition is adapted for intra-brain administration.

The term "carrier" refers to a diluent, adjuvant, excipient, or vehicle with which the active agent is administered. The carriers in the pharmaceutical composition may comprise a binder, such as microcrystalline cellulose, polyvinylpyrrolidone (polyvidone or povidone), gum tragacanth, gelatin, starch, lactose or lactose monohydrate; a disintegrating agent, such as alginic acid, maize starch and the like; a lubricant or surfactant, such as magnesium stearate, or sodium lauryl sulphate; and a glidant, such as colloidal silicon dioxide.

The compositions may be formulated for parenteral administration by injection, e.g., by bolus injection or continuous infusion. Formulations for injection may be presented in unit dosage form, e.g., in ampoules or in multidose containers, with an added preservative. The compositions may take such forms as suspensions, solutions or emulsions in oily or aqueous vehicles, and may contain formulatory agents such as suspending, stabilizing and/or dispersing agents. Alternatively, the active ingredient may be in powder form for constitution with a suitable vehicle, e.g., sterile pyrogen free water, before use.

For administration by inhalation, for example for nasal administration, the compositions according to the present invention are conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of, e.g., gelatin, for use in an inhaler or insufflator may be formulated containing a powder mix of the compound and a suitable powder base such as lactose or starch.

In certain embodiments the pharmaceutical composition is formulated for administration by any known method as described above. Particular methods of administration contemplated here are intravenous and intra-brain (intracerebral) administration.

The pharmaceutical composition according to any one of the embodiments defined above may be formulated for intravenous, intra-brain (intracerebral), oral, intradermal, intramuscular, subcutaneous, transdermal, transmucosal, intranasal or intraocular administration.

In yet another aspect the invention provides use of an active agent according to any one of the embodiments defined above that is capable of reducing quinone reductase 2 activity, for preparation of a medication for improving cognition. The active agent and quinone reductase 2 are as defined herein above, as is the definition for cognition, learning, memory and improvement thereof. In one embodiment the active agent is a nucleic acid molecule that reduces the gene expression level of quinone reductase 2. In another embodiment the active agent is an inhibitor of quinone reductase 2 activity. In certain embodiments a nucleic acid molecule encoding an siRNA or shRNA molecule comprising a sequence being complementary to a sequence within a nucleic acid sequence encoding human quinone reductase 2 may be used for the preparation of a vector for improvement of cognition in a subject in need thereof. Such a vector may be a viral or non-viral vector.

According to yet another aspect the present invention provides a method for improving cognition in a subject in need thereof comprising administering to said subject an active agent, a vector or a pharmaceutical composition as defined hereinabove. In some embodiments, the method comprises administration of a nucleic acid molecule that reduces the gene expression level of quinone reductase 2 or a vector comprising said nucleic acid molecule. In some particular embodiments the active agent is a viral vector that is a modified lentivirus comprising a nucleic acid molecule encoding an shRNA molecule comprising a sequence being complementary to a sequence within a nucleic acid sequence encoding human quinone reductase 2. In other embodiments the method comprises administering an active agent that inhibits said quinone reductase 2 activity, and said subject in need thereof does not include a subject treated with scopolamine.

The invention will now be illustrated by the following non-limiting Examples.

EXAMPLES

Material and Methods (M&M)

Subjects—Adult male Wistar Hola rats (Harlan Laboratories, Jerusalem) within a weight range of 200-300 gr (corresponding to an age of 8 to 12 weeks) were used for this study. They were maintained on a 12 hour light/dark cycle and all experiments were carried out during the light cycle. Additionally, the rats had ad libtum access to food and water unless otherwise indicated. The procedures were performed in strict accordance with the University of Haifa regulations and the US National Institutes of Health guidelines (NIH publication number 8023).

The vehicle—In all of the experiments in which we utilized pharmacological agents they were prepared in physiological saline. Physiological saline was prepared in house by dissolving NaCl in DDW (0.9% w/v). The physiological saline was injected to the controls in all experiments in which the test group(s) was injected with a pharmacological agent. The same volume of the vehicle was injected as the pharmacological agent.

QR2 inhibitors—We used two inhibitors of QR2 activity, S29434 and S26695, obtained from Pharmacolgie Moleculaire et Cellulaire, Institut de Recherches Servier. The inhibitors were dissolved in dimethyl sulfoxide (DMSO) and then added to physiological saline. The final concentration of dimethyl sulfoxide in the physiological saline was 5%. These inhibitors were injected prior to the learning process intraperitoneally (i.p.) 10 mg/kg.

mAChR antagonist—In order to prevent the proper activation of muscarinic acetylcholine receptor (mAChR) we utilized (−)-Scopolamine hydro-chloride, (Sigma) a mAChR antagonist. The scopolamine was dissolved in DDW and added to physiological saline. The scopolamine was injected prior to the learning process i.p. 2 mg/kg.

Cholinesterase inhibitor—In order to prevent the breakdown of acetylcholine (Ach) we utilized eserine (aka physostigmine) (Sigma) a cholinesterase inhibitor. The eserine was dissolved in DDW and added to physiological saline. The eserine was injected prior to the learning process i.p. 1 mg/kg.

Tissue extraction—Following the learning protocol the insular cortex was removed by hand. The insular cortex was identified through cortical landmarks, the rhinal fissure and the medial cerebral artery. The insular cortex was immediately placed in liquid nitrogen and then stored at −80° C.

mRNA quantification—We used the RNeasy lipid tissue kit (QIAGEN) according to the manufacturer's instructions in order to extract the RNA. We then evaluated RNA concentration and purity using a nanodrop spectrophotometer.

The cDNA synthesis was accomplished using the High Capacity Reverse Transcription Kit (ABI) according to the manufacturer's instructions. The reaction was carried out in a total volume of 20 μl on 1000 ng of RNA.

The qPCR reaction was performed in a total volume of 10 μl on 10 ng of cDNA. We used the following TaqMan assays (Applied Biosystems): QR2 (Rn01434728_g1), NQO1 (RN00566528_m1), glyceraldehyde-3-phosphate dehydrogenase, GAPDH (Rn01775763_g1). The reactions were carried out per the manufacturer's instructions.

Real Time-PCR analysis was performed using the PCR System STEP-ONE plus (Applied Biosystems). Relative mRNA levels were calculated using the $\Delta\Delta C_t$ method using GAPDH as a normalizing gene: $\Delta\Delta C_t=[(C_t(\text{gene of interest})-Ct(GAPDH))$ of the untreated group$]-[(C_t(\text{gene of interest})-Ct(GAPDH))$ of the treated group]. The fold increase is then calculated as such: fold increase=$2-\Delta\Delta C_t$.

Micro-infusion—Rats were anesthetized with Equithesin (0.45 ml/100 g) (2.12% w/v MgSO4, 10% v/v ethanol, 39.1% v/v 1,2,-propranolol, 0.98% w/v sodium pentobarbital, and 4.2% w/v chloral hydrate), restrained in a stereotactic apparatus (Stoelting, USA) and injected bilaterally with a 10 mm 28 gauge injection cannula aimed at the rat gustatory cortex (anteroposterior, +1.2 mm relative to bregma; lateral, ±5.5 mm; ventral, −5.5 mm; (Paxinos and Watson, 1986). The injection cannula was connected via PE20 tubing to a Hamilton microsyringe driven by a micro-infusion pump (CMA/100; Carnegie Medicin). Micro-infusion was performed bilaterally in a 1.0-μL of APV volume per hemisphere delivered over 1 min. The injection cannula was left in position before withdrawal for an additional 1 min to minimize dragging of the injected liquid along the injection tract. To avoid lateral bias, animals were injected interchangeably between both sides. Following the microsurgery, animals were injected i.m. with antibiotic and were allowed to recuperate for one week.

Lentiviral vectors, infection and expression—We received three clones containing short hairpin RNA (shRNA) constructs directed against mouse QR2 from SIGMA-ALDRICH: TRCN0000305463, TRCN0000305394 and RCN0000305334, referred herein as v463, v394 and v334, respectively, and identified herein as SEQ ID: 5, 6 and 7, respectively. Following an evaluation of these clones as explained in Example 9, we chose the TRCN0000305394 clone. We also received from SIGMA-ALDRICH a clone containing a scrambled shRNA sequence to use as a control. The U6 promoted shRNA sequences were each subcloned into the lentiviral (LV) plasmid pFUGW for coexpression of shRNA driven by the U6 promoter with EGFP under control of the CMV promoter. The LV was produced according to the method elaborated upon by Lois et al. (2002), incorporated by reference as if fully disclosed herein.

In brief the cassettes containing the shRNA sequences, EGFP, and the promoters were cotransfected into the 293FT cell line (Invitrogen, Carlsbad, Calif., USA). They were allowed to express and form particles for 48 hours and then collected, purified and concentrated though a series of centrifugation steps. The particles were then dissolved in sterile PBS and stored at −80° C. until they were used. The lentivirus was injected into the IC as described above. Following the injection period the animals were given 7 days to recover and for the lentivirus to express. We confirmed shRNA expression through RT-PCR analysis as described above.

Generation of primary cortical cells—Cortex regions were dissected from 1- to 2-days old WSH rats, dissociated by trypsin treatment, followed by trituration with a siliconized Pasteur pipette, and then plated onto coverslips coated with polyethilenimine (Sigma, St. Louis, Mo.). Seeding culture medium consisted of MEM (Gibco without phenol red for microscopy), 20 mM glucose (sigma), Gentamycine Sulfate 5 µg/ml (sigma), 25 mg/l insulin (Sigma), 2 mM 1-glutamine (sigma), 5-10% fetal bovine serum (Sigma), and 10% NU serum (Becton Dickinson Labware). Cultures were maintained at 37° C. in a 95% air/5% $CO_2$ humidified incubator, and culture medium was replaced to feeding medium containing MEM (sigma) 20 mM glucose (sigma), Gentamycine Sulfate 5 µg/ml (sigma), and 2% B-27 (Gibco) and 0.5 mM L-glutamine supplement (Invitrogen) every 7 days.

Statistical analysis—The results of the experiments are expressed as means±standard error of the mean. For statistical analysis we used the unpaired Student's t-test, Levene's t-test for equality of variances, one-way ANOVA test with Fisher's Least Significance Difference post-hoc test, and repeated measures ANOVA. Significance was determined by using an α-level of 0.05. We used the SPSS Statistics v.20 (IBM) program to perform the statistical analysis.

Preference index—the preference index was calculated by the following equation [(total novel taste liquid ingested/(novel taste liquid ingested+water ingested))*100]. The higher the preference index (PI) the more the rat preferred the novel taste (Rosenblum et al., 1993).

Aversion index—the aversion index is calculated by the following equation [(total water ingested/(novel taste liquid ingested+water ingested))*100].

Conditioned Taste Aversion (CTA)—Two groups of rats were deprived from water for a period of 24 hours. This was followed by 3 days of restriction were the rats received two pipettes each filled with 10 ml of water for 20 minutes each day. On the fourth day both groups received two pipettes each filled with 10 ml of an unfamiliar tasting liquid, either saccharine (0.1% w/v) or NaCl (0.3% w/v), for 20 minutes. Forty minutes following the exposure to the novel liquid the rats in the experimental group received an injection of LiCl (prepared in double distilled water (DDW)) (2% bodyweight, intraperitoneally (i.p.)) and those in the control received an injection of physiological saline (2% bodyweight, i.p.).

LI-CTA learning paradigm. This paradigm presents the animal with a novel taste. The animal is then given 48 hours during which it will form a memory of the taste and will consider the taste to be a safe taste. The animal will then be presented with the taste again and then injected with LiCl in order to induce malaise. Normally when an animal is presented with a taste and then has malaise induced (CTA) the animal will form a very high aversion to that taste. However, when the animal has already learned the taste as a safe taste and then undergoes CTA the aversion to the taste will be diminished. The stronger the positive memory of the safe taste the lower the aversion index.

Example 1—Novel Taste Learning Induces a Reduction in the Level of QR2 mRNA in the Insular Cortex Rats underwent three days of water restriction, following which we gave the control group access to two pipettes containing 10 ml of water each for 20 minutes and the test group access to two pipettes containing 10 ml of 0.1% w/v saccharin for 20 minutes (novel taste) (the conditioned stimulus (CS)). Both groups were then injected with LiCl 0.15M (the unconditioned stimulus (UCS)) i.p. 40 minutes following the drinking period. There was no significant difference between the amounts consumed by each group (unpaired Student's t-test, $t_{16.920}$=0.123, n=10, P>0.05). The animals were then sacrificed 4.5 hours later in order to evaluate changes in mRNA expression. RNA from the IC was extracted and used as a template to synthesize cDNA. We sent this cDNA to be evaluated using a microarray (Affymetrix® rat gene 1.1 St Array plate) to compare changes in gene expression in the group which learned to associate the taste with malaise as opposed to the group which did not undergo a learning paradigm. We found that there was about 50% reduction in QR2 mRNA expression in the group which learned to associate the taste with malaise as opposed to the control group which did not undergo any taste learning (n=4, P<0.05)

These results were validated using RT-PCR which is a more direct method for evaluating changes in mRNA expression. Additionally, we increased the sample size to ensure the reliability and significance of the results. The results from this experiment (FIG. 1) show that associative taste learning leads to about 45% decrease in QR2 mRNA expression in the IC compared to the control group. These results confirm the results from the microarray screen that in animals given a UCS and a CS, there is a significant reduction in QR2 mRNA expression compared to the control group, presented only with the UCS. This suggests that the reduction in QR2 expression is caused by associative learning (unpaired Student's t-test, $t_{10.39}$=4.3, n=10, p<0.005).

Example 2—Exposure to a Novel Taste Induces a Reduction in QR2 mRNA Expression in the IC M&M—Two groups underwent three days of water restriction, following which we gave the control group access to two pipettes containing 10 ml of water each (a familiar taste) for 20 minutes and the test group access to two pipettes containing 10 ml of 0.1% w/v saccharin each (a novel taste) for 20 minutes. There was no significant difference between the amounts consumed by each group (unpaired Student's t-test, $t_{20}$=0.509, n≥10, P>0.05). Both groups were sacrificed 3 hours following the drinking period in order to evaluate biochemical changes.

Figure 2:
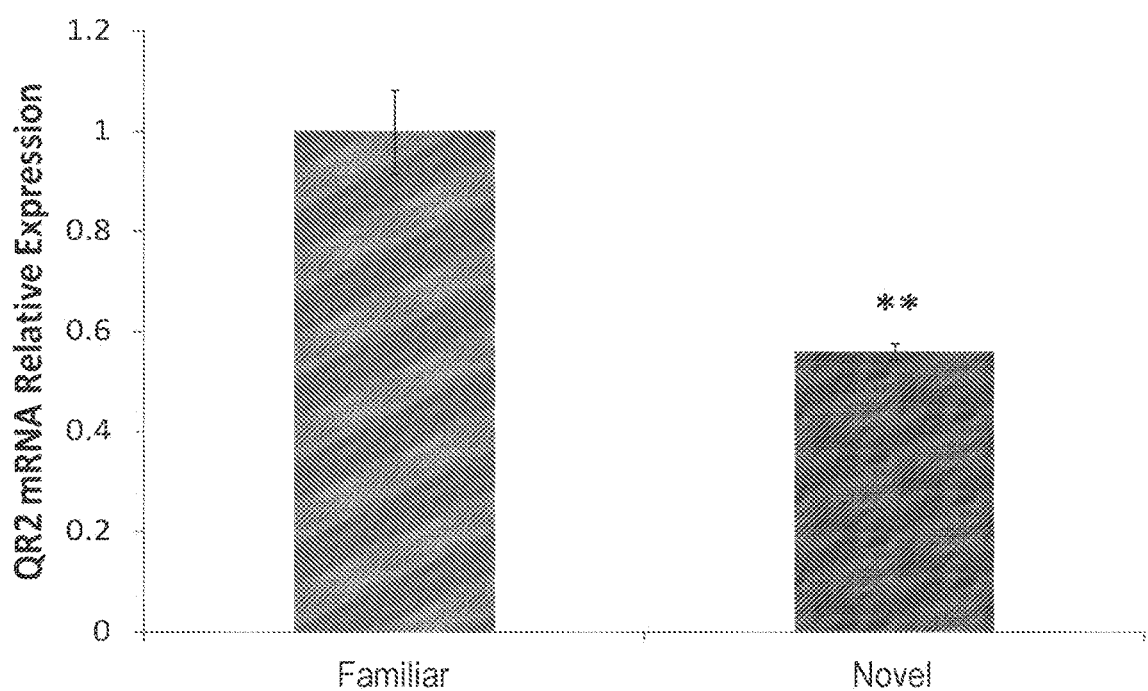
FIG. 2 shows that novel taste learning leads to a significant decrease in QR2 mRNA expression in the IC. Animals which learned a novel taste (saccharin) exhibited a ~45% decrease in QR2 mRNA expression in the IC when compared to the control group, which was only exposed to a familiar taste (tap water), and therefore did not undergo taste learning (unpaired Student's t-test, n≥10, **$p<0.005$; error bars represent SEM).

Results—To evaluate the hypothesis that the changes in QR2 mRNA expression in the IC following the associative taste learning seen in Examples 1 and were primarily due to the learning of a novel taste and not due to learning a taste association we isolated the variable factor from above. One group of animals learned a novel taste (saccharin) while the control group was presented with a familiar taste (water), and therefore did not undergo a taste learning paradigm (see M&M of this example). We then evaluated changes in QR2 mRNA expression in the IC three hours following the learning period using the RT-PCR method (FIG. 2) which showed that there is about 45% decrease in QR2 mRNA expression in the group which received a novel taste compared to the group which received a familiar taste. These results supported our hypothesis that novel taste learning induces a reduction in QR2 mRNA expression (unpaired Student's t-test, $t_{11.77}$=4.324, control-n=12 test-n=10, p<0.005).

Figure 3:
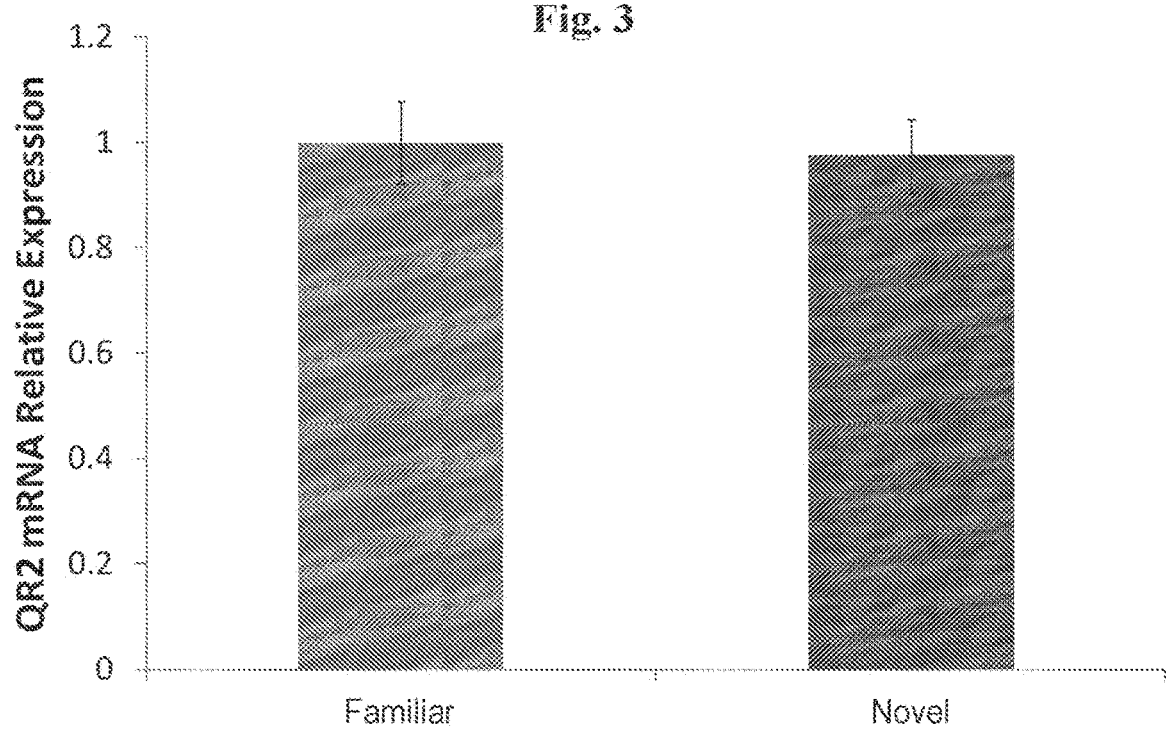
FIG. 3 shows that novel taste learning has no effect on the QR2 mRNA expression in the occipital cortex. There was no difference in QR2 mRNA expression in the occipital cortex between the group which received a novel taste (saccharin) to that which received a familiar taste (water) (unpaired Student's t-test, n=8, $p>0.05$; error bars represent SEM).
Figure 4:
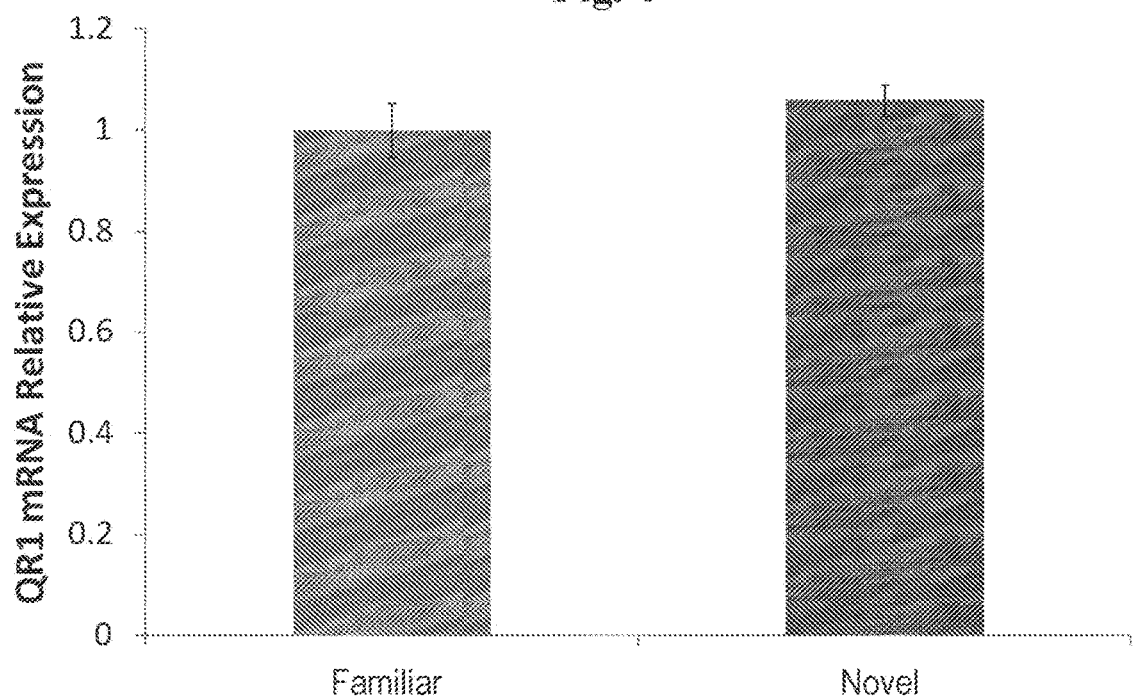
FIG. 4 shows that novel taste learning has no effect on QR1 mRNA expression in the IC. There was no difference in QR1 mRNA expression in the IC between the group which underwent novel taste learning to that which did not (unpaired Student's t-test, n=8, $p>0.05$; error bars represent SEM).

Example 3—The Changes in QR2 mRNA Expression Following Taste Learning are Specific to the IC To verify that the changes in QR2 mRNA expression were indeed due to learning, and therefore were only present in the relevant brain region, the insular cortex, in which the gustatory area resides, we evaluated changes in QR2 mRNA expression in the same animals in a non-relevant brain region, the occipital cortex. We determined that there were no differences in QR2 mRNA expression in the occipital cortex (FIG. 3) supporting our hypothesis that the changes are induced by novel taste learning and therefore specific to the IC (unpaired Student's t-test, $t_{13.89}$=0.144, n=8, p>0.05).

Figure 7:
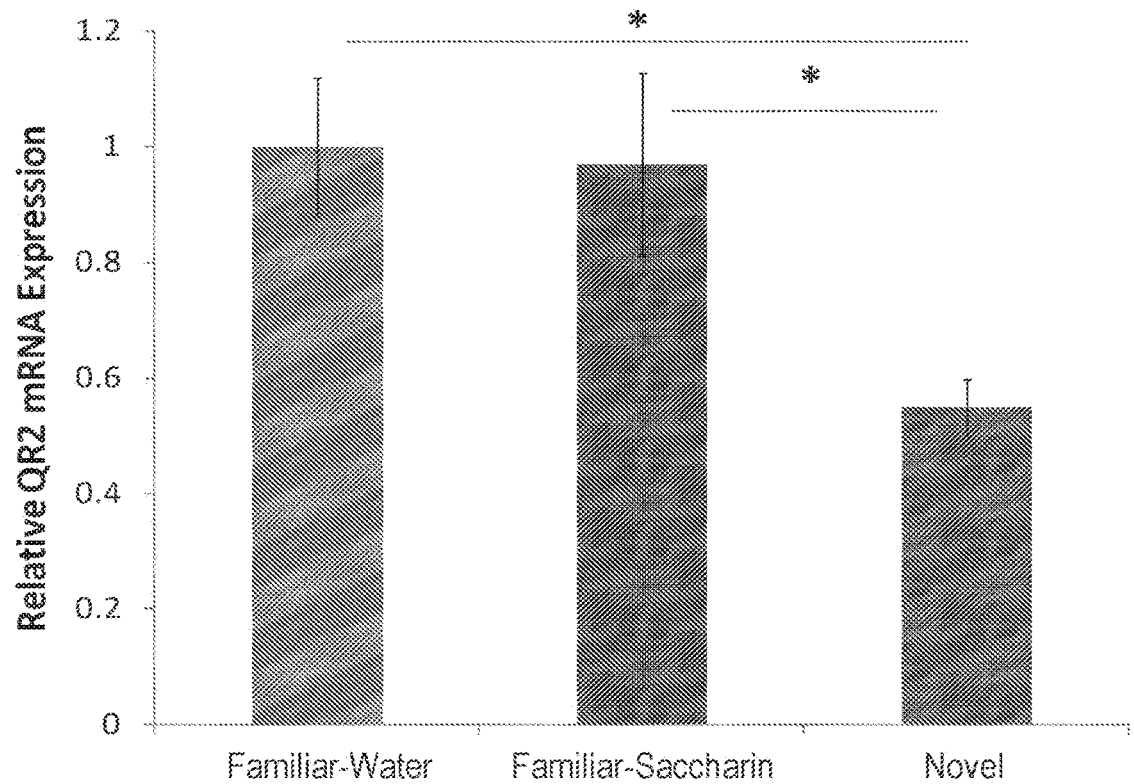
FIG. 7 shows that the novelty of the taste leads to a significant reduction in QR2 mRNA expression in the IC. The group which was exposed to the saccharin taste only once (a novel taste) had not only decreased QR2 mRNA expression in the IC compared to the group only exposed to water (a familiar taste) (one-way ANOVA with Fisher's Least Significant Difference post-hoc test, n=6, *p<0.05; error bars represent SEM) but also had decreased expression compared to the group which was familiarized to the saccharin taste (n=6, *p<0.05). Furthermore, there is no significant difference in QR2 mRNA expression in the IC between the group which only drank a familiar taste and the group which was sacrificed after drinking a taste to which it had been familiarized (n=6, p>0.05).

Example 4—There is No Change in QR1 mRNA Expression in the IC Following Exposure to a Novel Taste As mentioned above, QR2 is very similar to QR1 on a molecular level in terms of both nucleotide and amino acid sequence and in function (Vella et al., 2005). We therefore assessed whether the changes in QR2 mRNA expression following novel taste learning were specific to QR2 or also involved QR1. We found no difference in QR1 mRNA expression in the insular cortex between the group which underwent novel taste learning and the group which did not (unpaired Student's t-test, $t_{11.27}$=−0.788, n=8, p>0.05) and therefore concluded that the effect was specific to QR2 and that novel taste learning did not affect QR1 expression (FIG. 7).

Example 5—The Temporal Dynamics of QR2 mRNA Expression Following Novel Taste Learning M&M—Two groups of rats underwent three days of water restriction, following which we gave the control group access to two pipettes containing 10 ml of water each (a familiar taste) for 20 minutes and the test group access to two pipettes containing 10 ml of 0.1% w/v saccharin each (a novel taste) for 20 minutes. There was no significant difference between the amounts consumed by each group for 1 hour (unpaired Student's t-test, $t_{13}$=0.452, n>7, p>0.05), 3 hours ($t_{20}$=0.509, n≥10, P>0.05) and 6 hours ($t_{24}$=0.630, n=13, p>0.05. Both groups were then sacrificed at one of the time points noted above following the drinking period (1 hr; 3 hr; 6 hr) in order to evaluate biochemical changes.

Results—Having determined that there is a significant decrease in QR2 mRNA expression three hours following novel taste learning we decided to examine QR2 mRNA expression in the IC at additional time points. Therefore, we chose a time point towards the beginning of the consolidation period (one hour following learning) and a time point in the later stages of the consolidation period (six hours following learning). We compared QR2 mRNA expression between the group which underwent novel taste learning and the group which did not at these different time points following the drinking period to analyze the temporal dynamics of the changes in QR2 mRNA expression in the IC.

Figure 5:
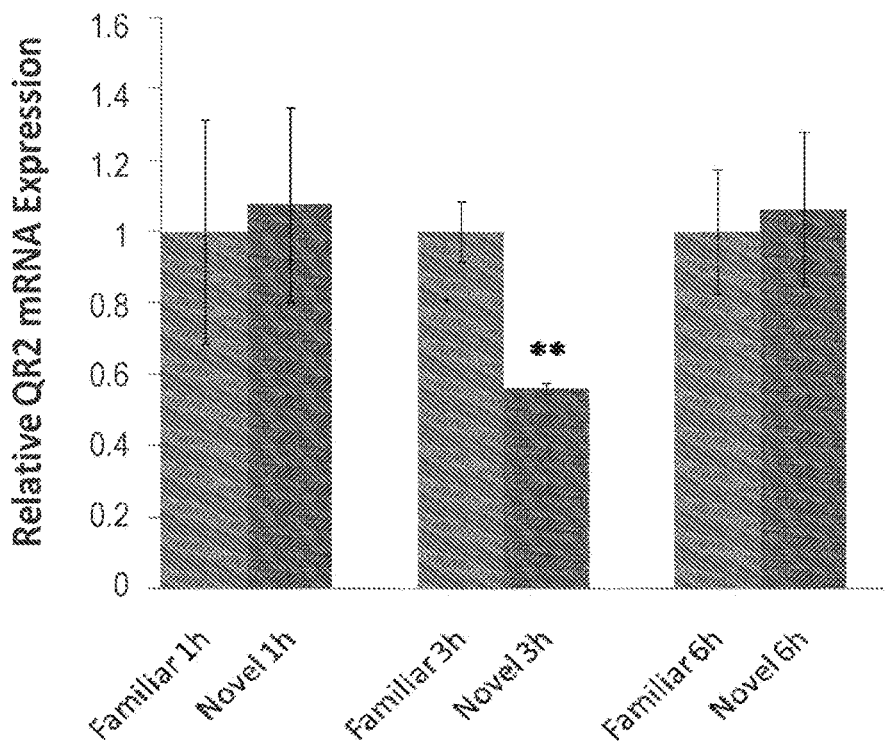
FIG. 5 shows that novel taste learning leads to a reduction in QR2 mRNA expression in the IC 3 hours following the learning period compared to the control group (unpaired Student's t-test, control-n=12 test-n=10, **$p<0.005$; error bars represent SEM). However, there is no difference between the groups 1 hour (control-n=7 test-n=8, $P>0.05$) or 6 hours after the drinking period (n=13, $p>0.05$).

We determined that while there is no difference in expression after one (unpaired Student's t-test, $t_{12.399}$=−0.209, control-n=7 test-n=8, p>0.05) or six hours following the drinking period ($t_{22.938}$=−0.040, n=13, p>0.05), there is a significant, about 45%, reduction in QR2 mRNA expression three hours ($t_{11.77}$=4.324, control-n=12 test-n=10, p<0.005) following novel taste learning (FIG. 5).

Example 6—Novel Taste Learning Leads to a Reduction in Expression of QR2 mRNA Compared to Baseline M&M—Three groups of rats underwent three days of water restriction, following which we gave one group access to two pipettes containing 10 ml of water each (a familiar taste) for 20 minutes and the second group access to two pipettes containing 10 ml of 0.1% w/v saccharin each (a novel taste) for 20 minutes. The third group was not given access to any liquid in order to serve as a baseline group. There was no significant difference between the amounts consumed by each group (unpaired Student's t-test, $t_{10}$=−0.758, n=6, p>0.05). All three groups were then sacrificed three hours after the drinking (or non-drinking) period.

Figure 6:
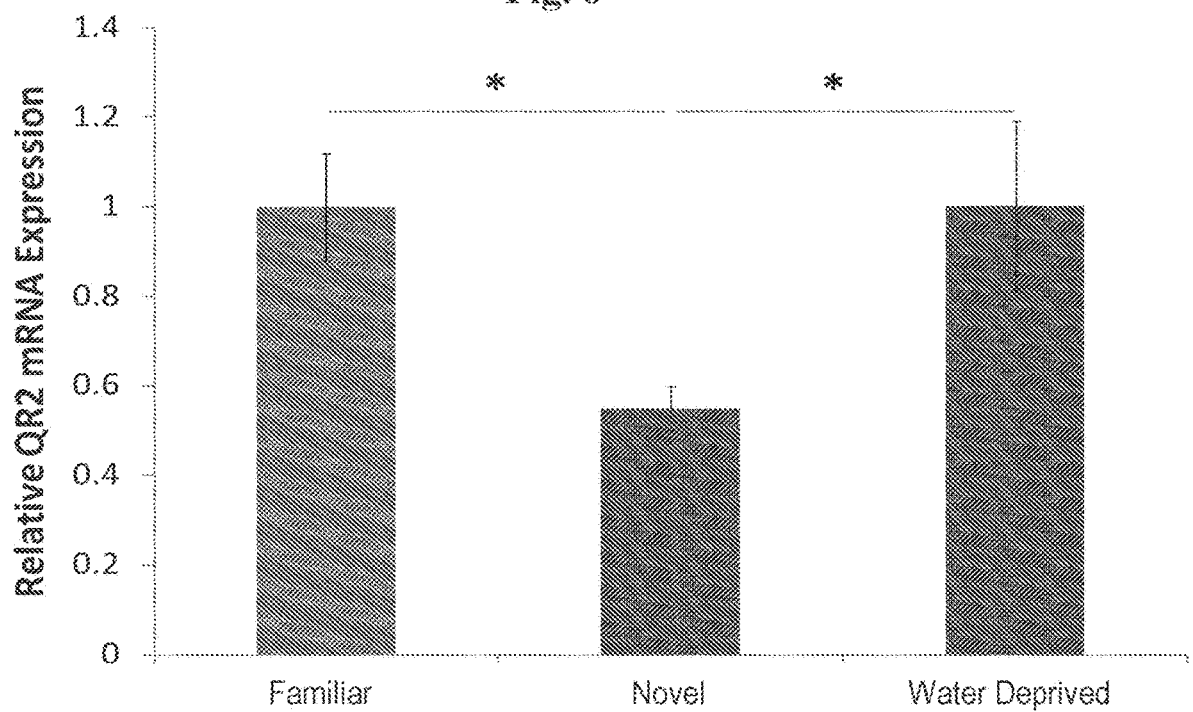
FIG. 6 shows that novel taste learning leads to a significant decrease in QR2 mRNA expression in the IC compared to baseline levels. The group which underwent novel taste learning not only had decreased QR2 mRNA expression in the IC compared to the group exposed to a familiar taste (one-way ANOVA with Fisher's Least Significant post-hoc test, n=6, *$p<0.05$; error bars represent SEM) but also had decreased expression compared to the water deprived/baseline group (n=6, *$p<0.05$). Moreover, there was no significant difference in QR2 mRNA expression in the IC between the baseline group and the group exposed only to a familiar taste (n=6, $p>0.05$).

Results—In order to elucidate whether the drinking per se or the novel taste learning leads to a decrease in QR2 mRNA expression in the IC we designed an experiment in which we added a third group in which the animals were prevented from drinking for a period of 24 hour prior to sacrifice, allowing them to act as a baseline to which to compare the other two groups. We determined that the QR2 mRNA expression in the IC in the animals, which had not been drinking and which were serving as our baseline, was most similar to those of the animals in the group which had received the familiar taste (FIG. 6; one-way ANOVA $F_{2.15}$=3.867, n=6, p<0.05). There was no significant difference between the group which was water deprived and the group which received a familiar taste (Fisher's Least Significant post-hoc test p>0.05) There was a significant about 45% reduction in QR2 mRNA expression in the IC of the group which had undergone novel taste learning compared to the baseline group (Fisher's Least Significant post-hoc test p<0.05).

Example 7—The Novelty of the Taste Leads to the Reduction in QR2 mRNA Expression in the Insular Cortex and Not the Taste Itself M&M—Two groups, the familiar-water group and the novel taste group, had unlimited access to water until the final five days of the experiment. They then had three days of restricted access to water, following which the familiar-water group was given access to two pipettes containing 10 ml of water each (a familiar taste) for 20 minutes. The novel taste group was given access to two pipettes containing 10 ml of 0.1% w/v saccharin each (a novel taste) for 20 minutes. The third group, the familiar saccharin group, had unlimited access to 0.1% w/v saccharin for 24 days. They then had restricted access to 0.1% w/v saccharin for three days. Following the three day restriction period they were given access to two pipettes containing 10 ml of 0.1% w/v saccharin each (a novel taste) for 20 minutes. There was no significant difference between the amounts consumed by each group (one-way ANOVA $F_{2,15}=0.647$, n=6, p>0.05). All three groups were then sacrificed three hours after the final drinking period.

Results—To examine whether the chemical information of the taste itself or the novelty of the taste causes the decrease in QR2 mRNA expression in the IC we carried out an experiment with three groups (as described in the M&M part of this Example) The results support that the learning of the novel taste is the factor which induces the decrease in QR2 mRNA expression in the IC (FIG. 7; one-way ANOVA $F_{2,15}=4.577$, n=6, p<0.05). The two groups which were sacrificed after being exposed to a familiar taste, either water or saccharin, had similar levels of QR2 mRNA expression in the IC (Fisher's Least Significant Difference post-hoc test p>0.05). However, the group of rats sacrificed following learning a novel taste expressed significantly decreased levels of QR2 mRNA in the IC compared to both the group which received only water (p<0.05) and the group which was familiarized to the saccharin taste (p<0.05).

Example 8—Novel Taste Learning Leads to a Reduction in the Variance of QR2 mRNA Expression in the IC in Addition to the Decrease in Expression We noticed that in all the above experiments in which QR2 mRNA expression in the IC was reduced following taste learning (FIGS. 1, 5, 6 and 7), the groups which did not undergo taste learning exhibited more variation in QR2 mRNA expression levels than the test group. We determined, using Levene's Test for Homogeneity of Variances, that there was a significantly higher level of variation in all of the groups which did not undergo taste learning compared to the group which did undergo taste learning; which are (a) the group exposed to only the UCS ($F_{1,18}=11.661$, n=10, p<0.005), (b) the group which was presented with a familiar taste and sacrificed 3 hours later ($F_{1,20}=15.464$, control-n=12 test-n=10, p<0.005), (c) the group which was presented with a familiar taste and sacrificed 24 hours later ($F_{1,10}=19.441$, n=6, p<0.005), (d) the group which was water deprived ($F_{1,10}=6.599$, n=6, p<0.05), and (e) the group which was familiarized to saccharin ($F_{1,10}=10.403$, n=6, p<0.01).

Example 9—Evaluation of the Efficacy of the QR2 shRNA Clones

Following our previous results we hypothesized that decreasing QR2 mRNA expression in the IC would enhance the animal's ability to form taste memories for two reasons: firstly, we conjectured that if taste learning leads to a decrease in QR2 mRNA expression, then the a priori decrease of QR2 mRNA expression will enhance taste memory. Secondly, as noted above, QR2 knocked-out (KO) mice showed enhanced cognitive function in hippocampal dependent tasks (Benoit et al., 2010).

Figure 8:
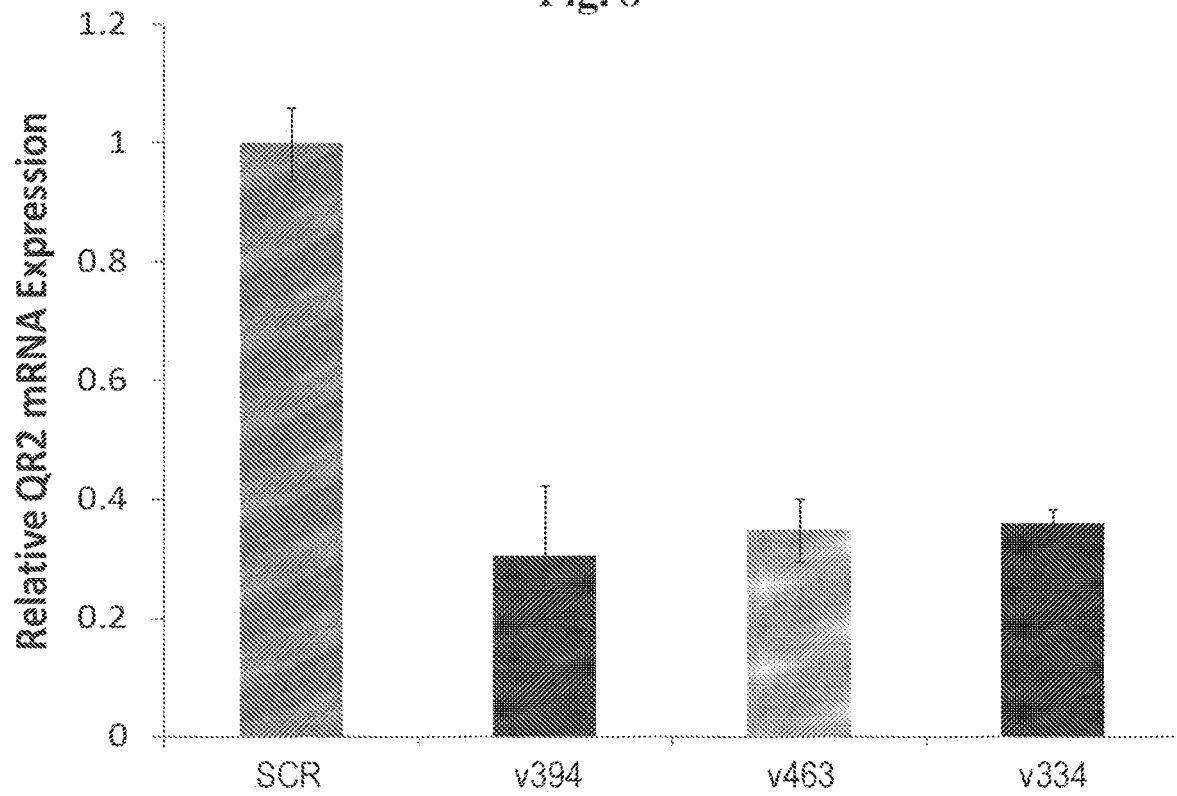
FIG. 8 shows that lentiviral vectors expressing QR2 shRNA reduces QR2 expression in primary cortical cells. Rat primary cortical cells were prepared as described in the M&M part. The primary cells were then treated with one of the virus types. Following a week long incubation period, cells were gathered, and QR2 mRNA expression was evaluated. The viruses containing QR2 shRNA reduced QR2 expression in primary cortical cells compared to the scrambled virus.

In order to evaluate our hypothesis that reducing QR2 mRNA expression in the IC will enhance positive taste learning, we prepared a virus expressing QR2 shRNA. For this purpose, we evaluated three different clones (Sigma-Aldrich, Israel). We tested the ability of these clones to reduce QR2 mRNA expression by applying them to primary cells as described above. We then evaluated QR2 mRNA expression. These results indicated that all clones were effective in decreasing QR2 mRNA expression but one was slightly more effective (FIG. 8). We therefore used that clone (v394) to prepare a virus (vector) for injection into rats as described above.

Figure 9:
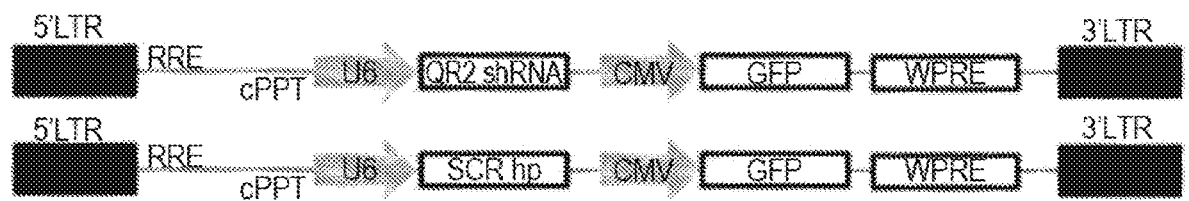
FIG. 9 shows the construct of the injected viruses. The virus illustrated in the top part of the figure is the one containing the QR2 shRNA which was used to decrease QR2 mRNA expression in the IC. The virus illustrated in the bottom part of the figure is the scrambled one which was used as a control.

Example 10—Reducing QR2 mRNA Expression in the IC Enhances Positive Taste Memory Having produced the virus, we then conducted an experiment containing two groups; one injected with a virus encoding the QR2 shRNA, and one injected with the scrambled virus (the control group) (FIG. 9). We then allowed the animals to recover from the injection process and for the virus to integrate. In this experiment, both groups, the group injected with the scrambled virus and the group injected with the shRNA virus, were given access to two pipettes containing 10 ml of 0.1% w/v saccharin each (a novel taste) for 20 minutes. There was no significant difference between the amounts consumed by each group (unpaired Student's t-test, $t_{22}=0.143$, n=12, P>0.05). Three days later the animals were given a choice test.

Figure 10:
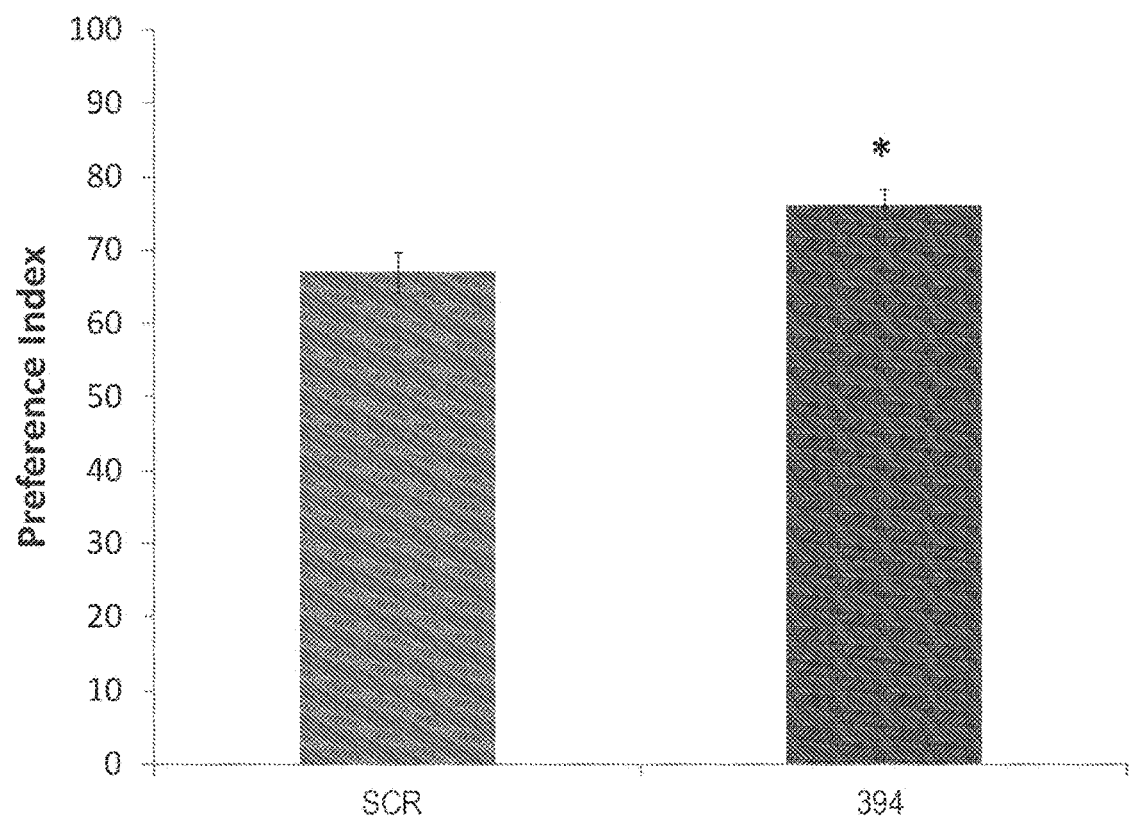
FIG. 10 shows that shRNA induced decrease in QR2 mRNA expression in the IC enhances positive taste memory. The animals which were injected with the shRNA reducing QR2 mRNA expression in the IC learned the novel taste better than the control group which was injected with the scrambled virus. This can be seen from the higher preference index (PI) in the shRNA group compared to the scrambled group (unpaired Student's t-test, $t_{21.063}$=-2.120, n=12, *p<0.05; error bars represent SEM).

The results (FIG. 10) show that reducing QR2 mRNA expression in the IC through the utilization of a lentiviral vector (LV) containing a QR2 shRNA enhances positive taste learning. The group which was injected with the QR2 shRNA virus had a higher preference index (PI) indicating that they learned the novel taste better than the control group which was injected with the scrambled virus (PI-scrambled=66.95+/−2.77, PI-394=76.3+/−2.14; unpaired Student's t-test, $t_{21.063}=-2.120$, n=12, p<0.05).

Figure 11:
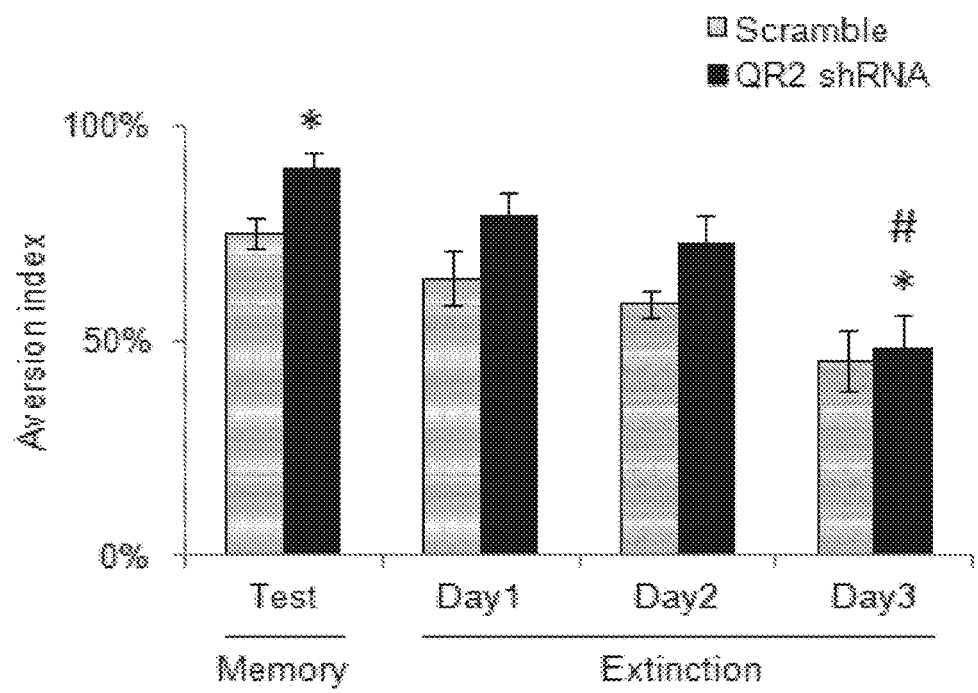
FIG. 11 shows the aversion index as a function of time following a CTA paradigm, from which the effect QR2 shRNA on memory extinction can be inferred.

Moreover, repeated measure ANOVA showed significant extinction on Day 3 in QR2 shRNA injected animals and no difference in extinction was evident in animals injected with scrambled shRNA (FIG. 11).

Figure 12:
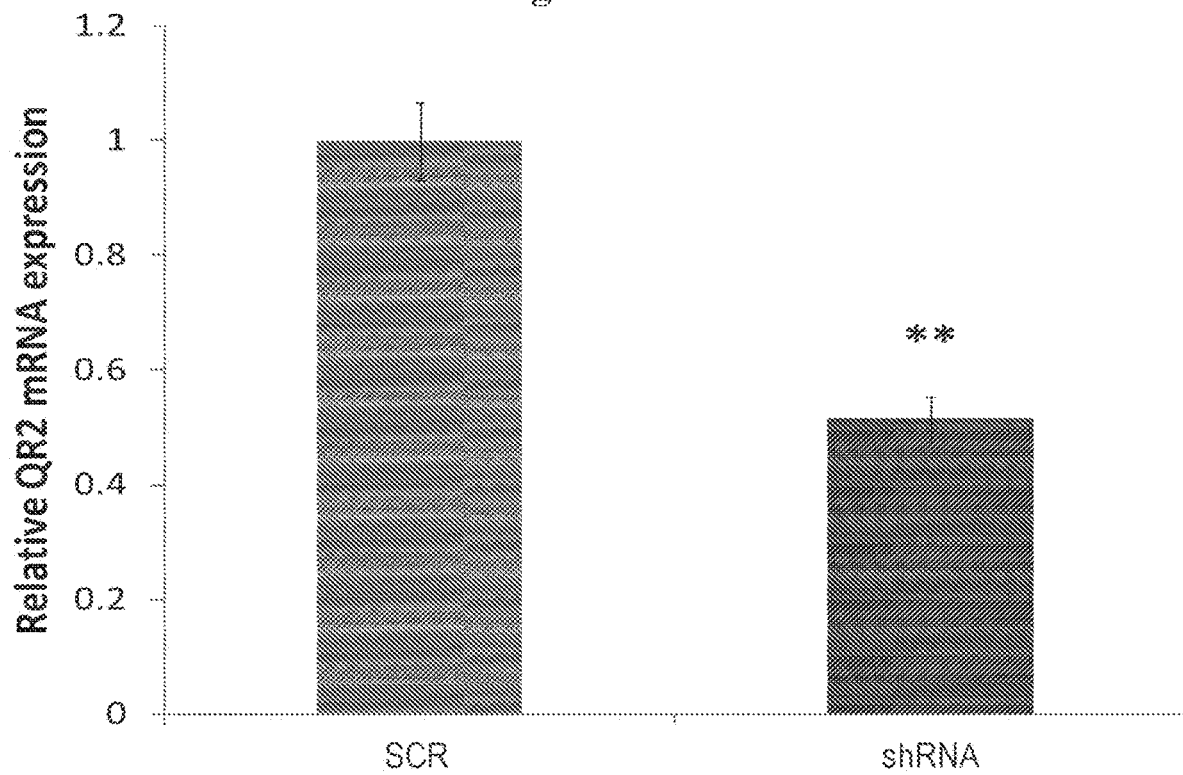
FIG. 12 shows that stereotactic injection of a virus expressing QR2 shRNA leads to a reduction in QR2 mRNA in the IC. We confirmed the efficacy of the virus injection by evaluating QR2 mRNA expression in the IC. The figure demonstrates that the shRNA virus was effective in decreasing QR2 mRNA expression in the IC compared to the control group which was injected with the scrambled virus (unpaired Student's t-test, $t_{17.6703}$=3.626, n=12, **p<0.005; error bars represent SEM).

Example 11—Injection of QR2 shRNA Carrying Virus Leads to Reduction in the Level of QR2 mRNA Following the preference test which demonstrated that the group which was injected with the QR2 shRNA virus has enhanced positive taste learning, we confirmed that the shRNA virus was effective in reducing QR2 mRNA expression in the IC compared to the control group which was infected with the scrambled virus. The results (FIG. 12) show that the group injected with the QR2 shRNA virus had significantly lower QR2 mRNA expression in the IC (unpaired Student's t-test, $t_{17.6703}=3.626$, n=12, p<0.005).

Example 12—Reducing the Expression of QR2 in Hippocampus Enhanced Learning and Memory as Shown in Delay Fear Conditioning Test M&M—A delay fear conditioning test was performed on two groups of mice (10 mice per group) injected with Lentivirus encoding the QR2 shRNA or a scrambled sequence one week before the experiment. The Lentivirus was injected in to the CA1 region of hippocampus. The conditioning apparatus used was four New Biotechnology Ltd. (NBT) chambers, (Panlab Harvard Apparatus, Barcelona, Spain) consisting of a Plexiglas walls (25×25×25 cm) with a 16 stainless steel rods grid floor, a dim light and speakers. The apparatus was located inside a sound proof larger, insulated plastic cabinet that excluded outside light and noise. On day 1 (training), the mice were transported to the nearby testing room and set next to the conditioning chambers for a 5 min resting period with lights off. Each chamber was wiped with 30% ethanol solution before training and each mouse was placed in the chamber individually during training. For delay fear conditioning, mice were pre-exposed to an experimental chamber for 5 min, and received 5 trials in which 4000 Hz, tone, applied for 10 seconds at 76 dB (conditioned stimuli; CS) co-terminated by a 0.36 mA foot shock applied for 2 second (unconditioned stimuli; US), separated by 3.5 min inter-trial interval (ITI). After the last training trial, the mice were left in the conditioning chamber for another 120 s and were then placed back in their home cages.

On day 2 and day 8 (1 week later) (context fear test), the mice were returned to the same experimental chamber with the same contextual configuration for 10 min. Freezing behavior was recorded. On the third day and day 9 (1 week later) (tone fear test), the mice were set next to the conditioning chambers for a 5 min resting period with lights on, then mice were placed into the same experimental chamber, with novel contextual configuration (no light, and a smooth black Plexiglas floor), for 5 min during which freezing was record under infra-red light source. This was followed by 5 exposures to the 10 s, 4000 Hz tone, separated by 3.5 min ITI to test conditioned fear of the CS tone in the absence of contextual cues associated with shock. No shocks were administered. The chamber was wiped with 0.5% ammonia hydroxide between successive sets of mice, in order to provide novel environment. The software reports freezing behavior to the tone as percent freezing across all 5 trials. The animals' behavior was recorded, and the data analyzed by Freeze Frame 3.0 software (Coulbourn Instruments, PA, USA). The indication for fear memory was freezing.

Figure 13A:
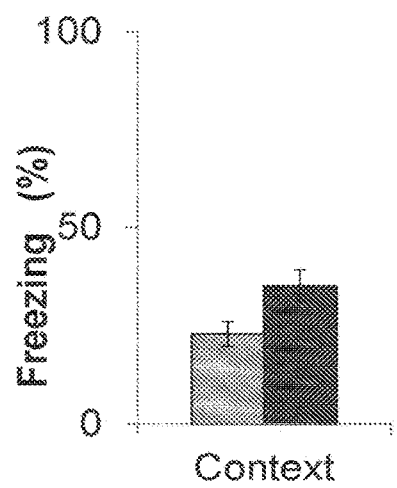
FIGS. 13A to 13D show that specific knockdown of QR2 in hippocampus (CA1 region) enhanced delay fear conditioning performance in mice.
Figure 13B:
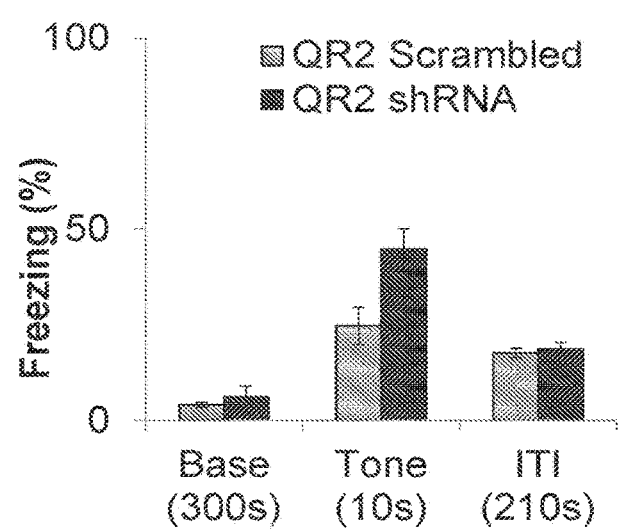
Figure 13C:
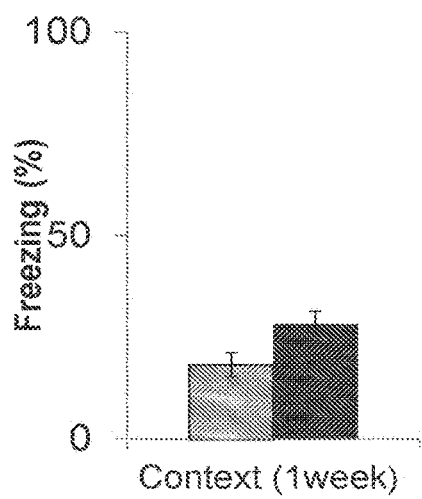
Figure 13D:
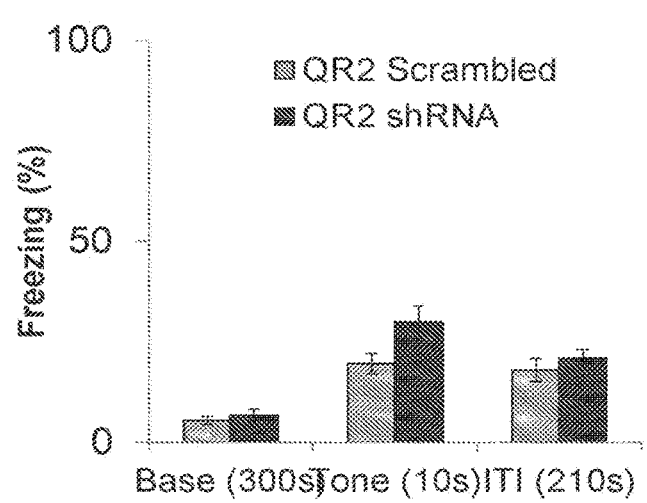

Results—The classical fear conditioning is being used to represent the neurobiology of learning and memory in addition to fear and anxiety. Data from delay conditioned animals was analyzed for baseline, tone, and context freezing. It can be clearly seen from FIG. 13 that reduction of quinone reductase 2 (QR2) in the CA1 region of hippocampus enhanced learning abilities in delay fear conditioning test. The QR2 shRNA injected mice froze significantly frequently than mice injected with the scrambled sequence during both the tone and context test (Context on day 2; $t18=-2.344$, p=0.031, Tone period on day 3; $t18=-3.481$, p=0.003 paired t-test, FIG. 13A-B). Moreover, QR2 shRNA injected mice showed enhanced long term memory after 1 week as follows from their response to conditioned context and tone exposure (context 1 week later; $t18=-2.350$, p=0.03, tone 1 week later; $t18=-2.347$, p=0.031 paired t-test, FIG. 13C-D)

Example 13—Reducing the Expression of QR2 in Hippocampus Enhanced Learning as Tested Using Morris Water Maze M&M—Spatial reference memory in the Morris Water Maze (MWM) was determined as previously described (Vorhees, Williams 2006). The pool was 1.2 m in diameter and the water was rendered opaque by the addition of white tempera. Water temperature was kept at 22° C. The platform was 8 cm in diameter. All behavioral tests and trials were performed at the same time of day (±1 hr) during the animal's light phase. The mice were acclimatized in testing room for 15 min. Mice were trained in four trials per day (trial length 60 s with 30 s ITI), over 4 consecutive days. If an animal fails to locate the platform within training time, it is usually picked up and placed on the platform for 15 s. For probe trials, the platform was removed from the maze and the animals were allowed to search for 60 s. Learning was evaluated by monitoring escape latencies to a hidden (submerged) platform and time spent in each quadrant of the maze (quadrant occupancy) with an automated video tracking system, and the data analyzed by EthoVision XT9 (Noldus Information Technology, USA). Swimming speed was similar in QR2 shRNA and scrambled injected animals (data not shown).

Figure 14A:
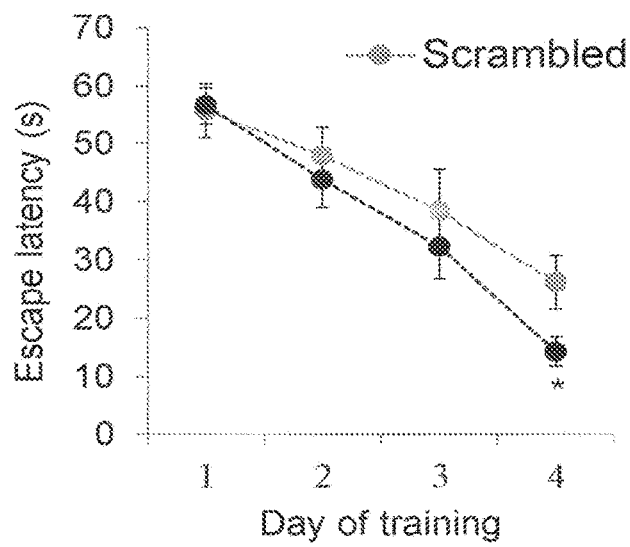
FIGS. 14A to 14C show that a knockdown of QR2 in hippocampus (CA1 region) enhances spatial memory in mice as tested by Morris Water Maze.
Figure 14B:
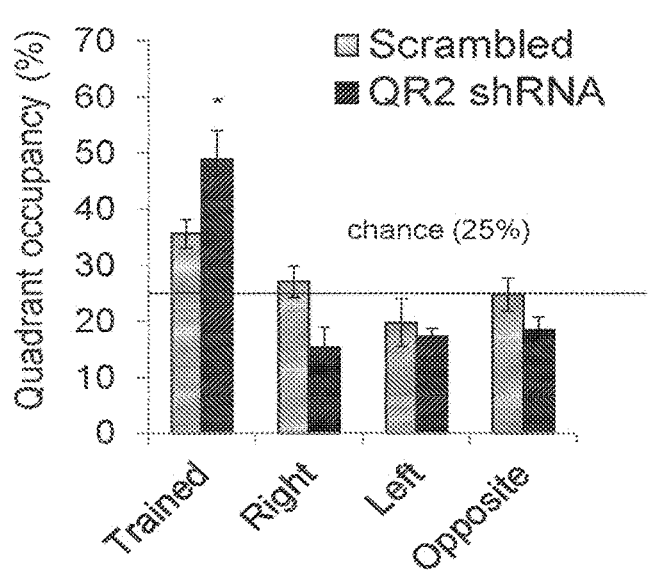
Figure 14C:
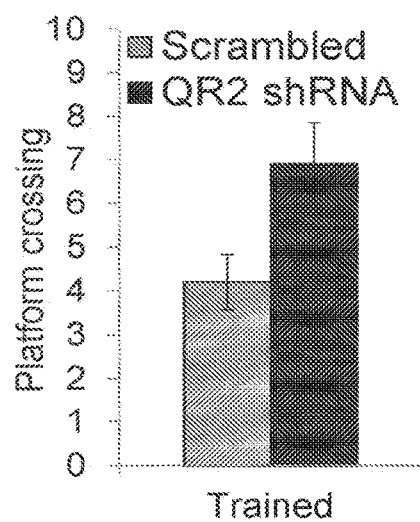

Results—As can be seen from FIG. 14, QR2-shRNA injected mice demonstrated improved learning abilities in MWM by having a shorter latency to locate the hidden platform on days 4 in the spatial component of the test ($t18=-2.267$, p=0.036 paired t-test). A repeated measures ANOVA with a Greenhouse-Geisser correction determined that mean scores for escape latency of QR2 shRNA injected mice were statistically different between training days (F(2.216, 19.947)=16.932, p<0.00003). Post hoc tests using the Bonferroni correction revealed that QR2 shRNA injected mice perform better on day 3 and day 4 of training, which was statistically significant (day 3; p=0.035, day 4; p=0.00007). The QR2-shRNA injected mice also exhibited enhanced learning performance, as shown by the amount of time they spent in the target quadrant during the probe test ($t18=-2.345$, p=0.031 paired t-test) and the amount of time they crossed the platform location ($t18=-2.373$, p=0.029 paired t-test). CA1 specific knockdown of QR2 does not affect other brain area (Insular Cortex) related behaviors like conditioned taste aversion (CTA). Together, these data suggest a role for QR2 in cognitive behaviors with QR2 inhibitors possibly representing a novel therapeutic strategy toward the treatment of learning deficits.

Example 14—Inhibiting QR2 Activity Enhances Positive Taste Memory

M&M—Four groups of rats underwent three days of water restriction. One group was injected with the vehicle (physiological saline) i.p. and then an hour later underwent the conditional test aversion (CTA) protocol: they were given access to two pipettes containing 10 ml of 0.1% w/v saccharin each (a novel taste) for 20 minutes, forty minutes following the drinking period the animals were injected i.p. with LiCl (0.15M) in order to induce malaise. Three days later they were given a choice test. The second group was injected with the vehicle (physiological saline) i.p., the third group was injected with the QR2 inhibitor S29434 i.p., the fourth group was injected with the QR2 inhibitor S26695 i.p.; these three groups underwent the LI-CTA protocol an hour following the injection: they were given access to two pipettes containing 10 ml of 0.1% w/v saccharin each (a novel taste) for 20 minutes, 48 hours later they were given, for a second time, access to two pipettes containing 10 ml of 0.1% w/v saccharin each (a novel taste) for 20 minutes, forty minutes following the drinking period the animals were injected i.p. with LiCl (0.15M) in order to induce malaise. There was no significant difference between the amounts consumed by each group (one-way ANOVA $F_{3,28}=0.220$, n=8, p>0.05). Three days later they underwent four days of choice tests.

Figure 15A:
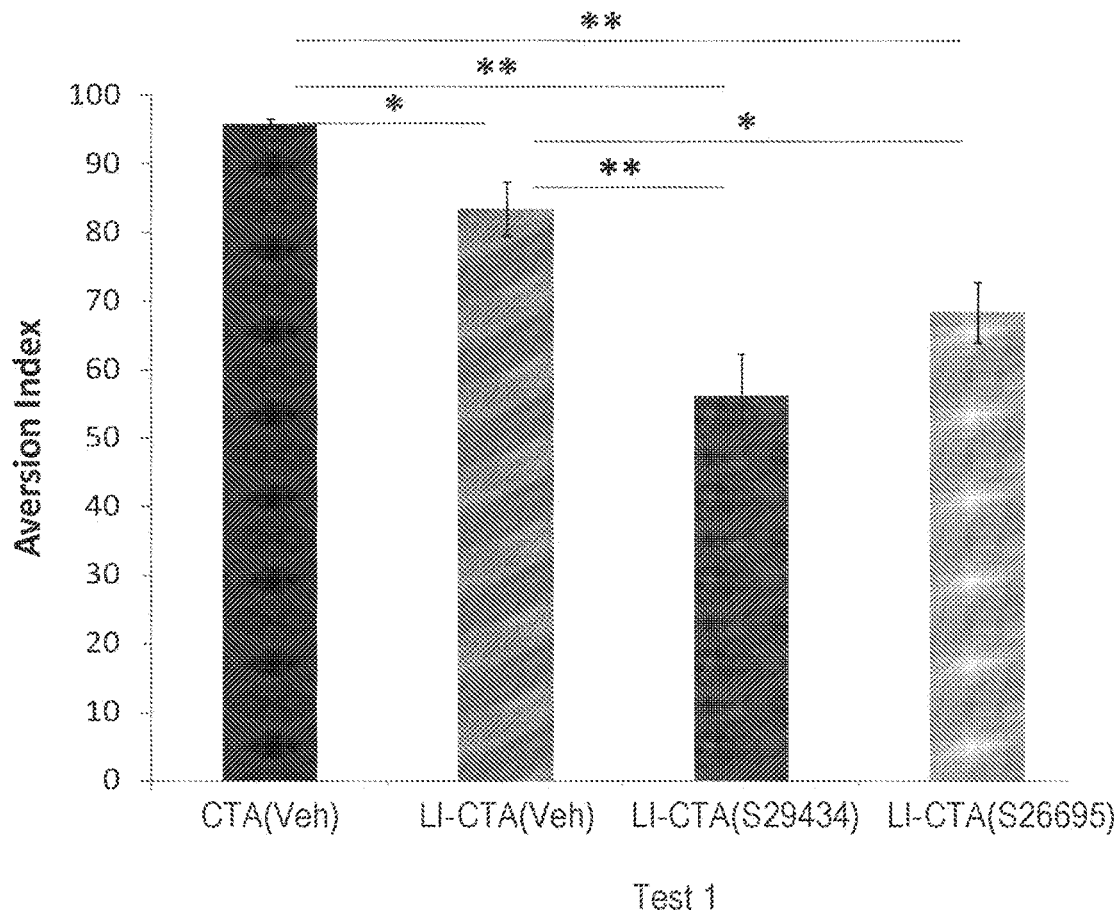
FIGS. 15A and 15B show that pharmacological inhibition of QR2 activity enhances positive taste memory.
Figure 15B:
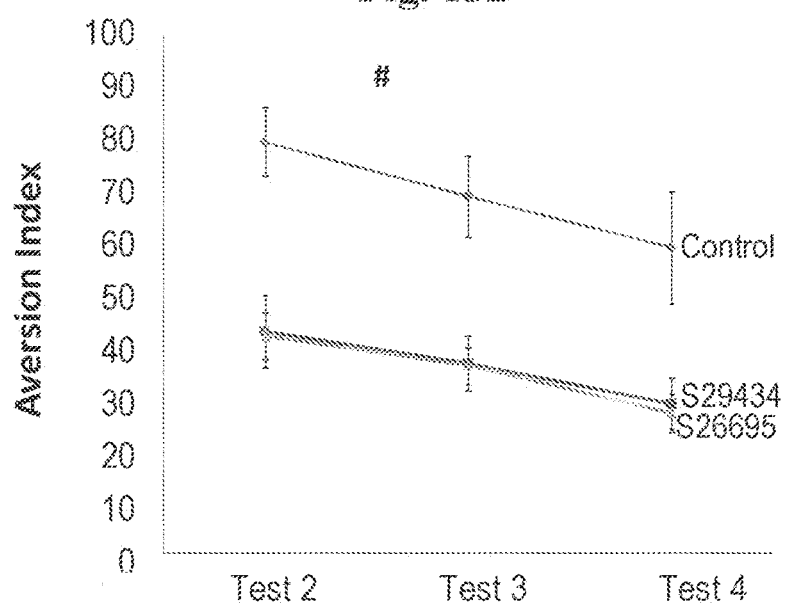

Results—FIG. 15A demonstrate that the inhibition of QR2 activity leads to the animal forming a stronger positive memory of the taste as being a safe taste (AI-CTA (veh)=94.06+/−0.99, AI-LICTA(veh)=83.47+/−3.83, AI-LICTA(S29434)=56.16+/−6.15, AI-LICTA (S26695)=68.44+/−4.44; one-way ANOVA $F_{3,28}=16.619$, n=8, p<0.001). The group which was injected with the vehicle before undergoing the LI-CTA protocol had significantly lower AI than the group which was injected with the vehicle before undergoing the CTA protocol (Fisher's Least Significant Difference post-hoc test, p<0.05). The group injected with S29434 before undergoing LI-CTA had a significantly lower AI than the group injected with the vehicle before undergoing CTA (p<0.001) and the group injected with the vehicle before undergoing LI-CTA (p<0.001). The group injected with S26695 before undergoing LI-CTA also had a significantly lower AI than the group injected with the vehicle before undergoing CTA (p<0.001) and the group injected with the vehicle before undergoing LI-CTA (p<0.05). There was no significant difference between the two groups which received the inhibitors (p>0.05). We also determined that the injection of the vehicle or inhibitor did not prevent the extinction process from occurring as can be seen from the lower levels of aversion on subsequent days of testing (FIG. 15B; repeated measures ANOVA with Greenhouse-Geisser correction $F_{2.420,48.409}=40.567$, n=8, p<0.001).

Example 15—Pharmacological Inhibition of QR2 Activity Enhances Negative Taste Memory M&M—We used three groups in this experiment, all of which were subjected to three days of water restriction. Following the three day water restriction period one group was injected with the vehicle; one group with S29434; one group with S26695. Then, one hour after the injections, all three groups were subjected to the CTA protocol: we gave them access to two pipettes containing 10 ml of 0.5% w/v NaCl each (a novel taste) for 20 minutes (in this experiment NaCl as the novel taste was used since CTA conducted with NaCl leads to a lower AI which prevents a ceiling effect from occurring and allows us to evaluate if the inhibitors generate an increase in learning and therefore a higher AI). Forty minutes later the animals in all three groups were injected with LiCl (0.03M) in order to induce malaise. There was no significant difference between the amounts consumed by each group (one-way ANOVA $F_{2,21}=0.376$, n=8, p>0.05). Three days later all the animals underwent four days of choice tests.

Figure 16A:
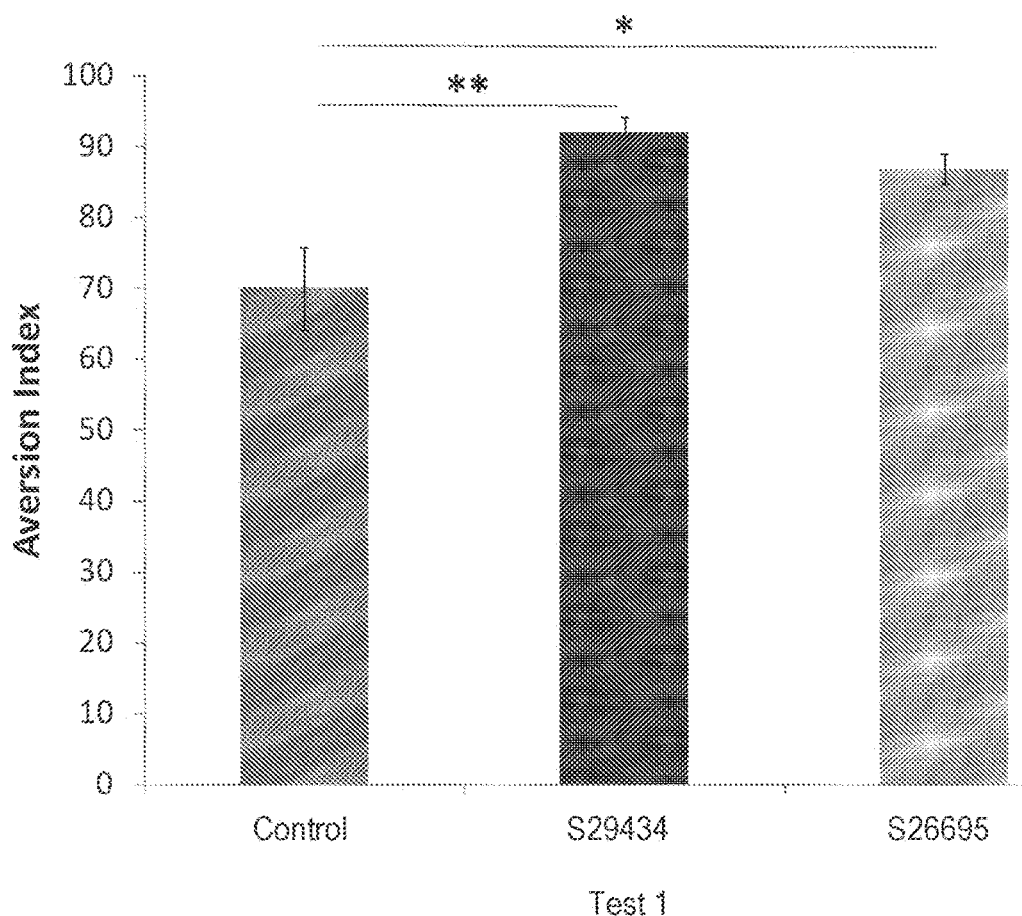
FIGS. 16A and 16B show that pharmacologic inhibition of QR2 activity enhances negative taste memory.
Figure 16B:
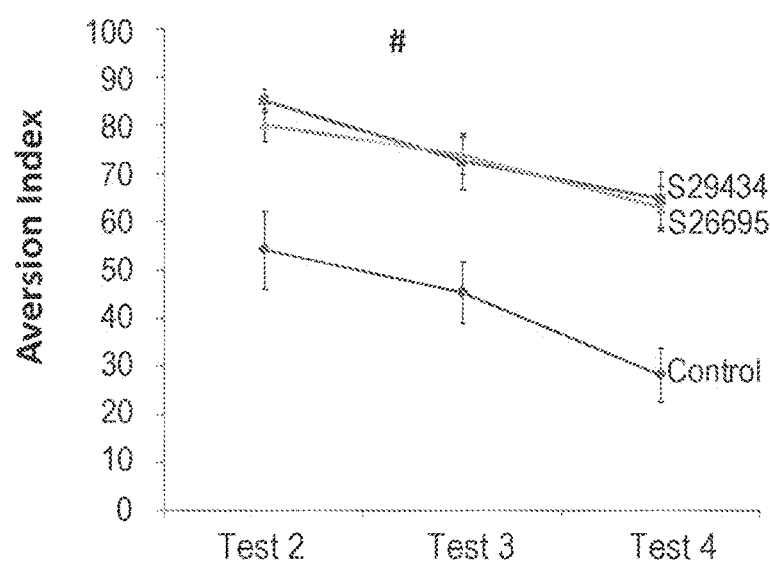

Results—FIG. 16A demonstrate that pharmacological inhibition of QR2 activity enhanced negative taste memory (AI-vehicle=70.04+/−5.85, AI-S29434=9201+2.15, AI-S26695=86.84+/−2.17; one-way ANOVA $F_{2,21}=9.074$, n=8, p<0.005). The group injected with S29434 before undergoing CTA had a significantly higher AI than the group which was injected with the vehicle before undergoing CTA (Fisher's Least Significant Difference Test p<0.005). The group injected with S26695 before undergoing CTA also had a significantly higher AI than the group which was injected with the vehicle before undergoing CTA (p<0.01). There was no significant difference between the two inhibitors in terms of their AI (p>0.05). We also determined that the injection of the vehicle or inhibitor did not prevent the extinction process from occurring as can be seen from the lower levels of aversion on subsequent days of testing (FIG. 16B; repeated measures ANOVA with Greenhouse-Geisser correction $F_{1.791,37.605}=42.465$, n=8, p<0.001).

Example 16—AD Patients Overexpress QR2 mRNA in the Frontal Cortex

M&M—Human samples were received from the Brain Bank at Mt. Sinai School of Medicine, New York, N.Y. The study included postmortem cross-sections of 39 nursing home residents with clinical dementia rating (CDR) scale scores ranging from CDR 0 (no dementia, n=11), to CDR1 (mild dementia, n=28). Brain samples were taken from the superior frontal gyrus (Bm8). To quantify the mRNA in the samples the total RNA (1 μg) from the superior frontal gyrus (Bm8) was reverse transcribed using ImpromII (Promega, WI) with random hexamers (MBI, Fermentas, Lithuania). Real time PCR was performed in a total volume of 10 μl using TaqMan universal PCR master mix (Applied Biosystems), using 2 μl of cDNA and gene specific "Assay on Demand" TaqMan reactions (Applied Biosystems). Real time PCR reactions were performed in duplicate using the ABI PRISM StepOne plus Sequence Detector (Applied Biosystems) under the following conditions: 50° C. for 2 min, 95° C. for 10 min, and 40 cycles of 95° C. for 15 s and 60° C. for 1 min. Threshold cycle (Ct) values of the examined gene of interest (QR2, Hs01056948_m1) were normalized to the Ct values of two housekeeping genes GUSB and IPO8 (Hs99999908-m1, Hs00183533-m1 respectively) in the AD and aged matched control groups. Relative mRNA quantities were calculated for each sample separately using $2^\wedge$-dct formula, and mRNA RQ for the test group (AD) was calculated using the $2^\wedge$-ddct formula. Statistical analysis were performed using $2^\wedge$-dct the values.

Figure 17A:
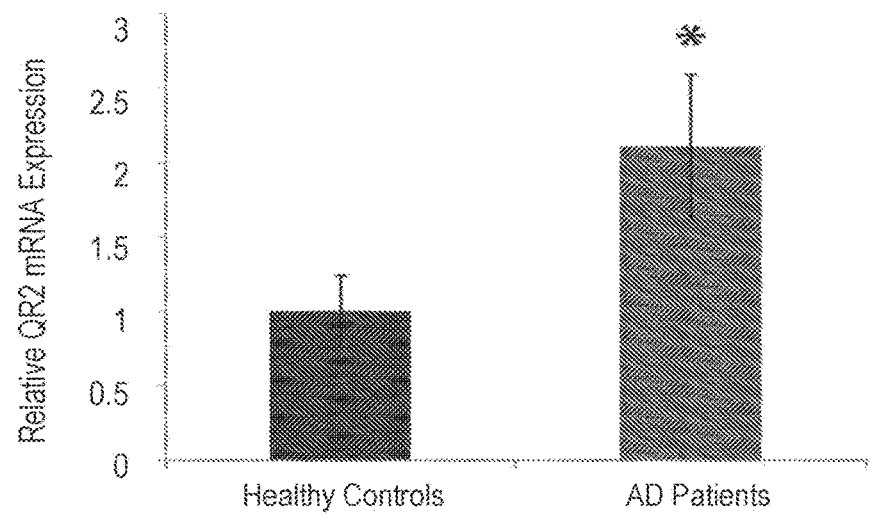
FIGS. 17A and 17B show that Alzheimer's disease (AD) patients overexpress QR2 mRNA in the frontal cortex.
Figure 17B:
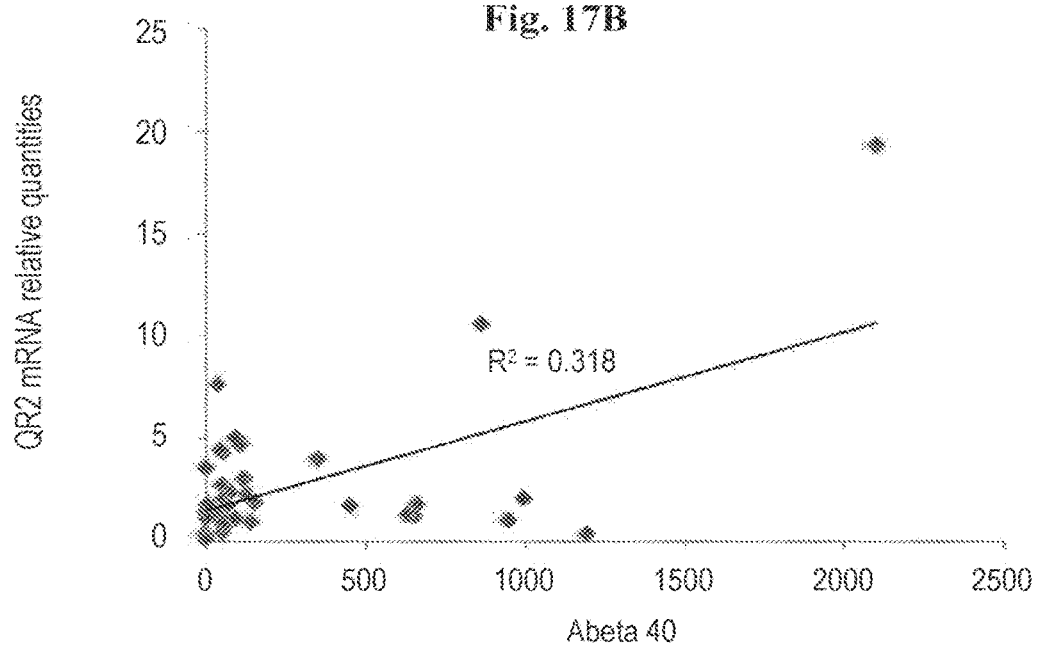

Results—It has been previously demonstrated that patients with Alzheimer's disease (AD) overexpress QR2 protein in the hippocampus. We measured cortical QR2 mRNA from demented (AD) and healthy aged matched controls. As it can be seen from FIG. 17A, AD patients express chronically higher levels of QR2 mRNA in the frontal cortex (Brodmann area 8). Interestingly, QR2 mRNA relative quantities were correlated with αβ-40 levels but not with other pathological factors, like TAU pathology, αβ-42 levels, plaque load, age, gender or the number of APOE ε4 alleles (FIG. 17B).

REFERENCES

Bailey, C. H., D. Bartsch, and E. R. Kandel. "Toward a Molecular Definition of Long-term Memory Storage." *Proc Natl Acad Sci USA* 93.24 (1996): 13445-3452. Print.

Benoit, C.-E., S. Bastianetto, J. Brouillette, Y. Tse, J. A. Boutin, P. Delagrange, T. Wong, P. Sarret, and R. Quirion. "Loss of Quinone Reductase 2 Function Selectively Facilitates Learning Behaviors." *Journal of Neuroscience* 30.38 (2010): 12690-2700. Print.

Brouillette, Jonathan, and Rémi Quirion. "Transthyretin: A Key Gene Involved in the Maintenance of Memory Capacities during Aging." *Neurobiology of Aging* 29.11 (2008): 1721-1732. Print.

Brouillette, J., D. Young, M. During, and R. Quirion. "Hippocampal Gene Expression Profiling Reveals the Possible Involvement of Homer1 and GABAB Receptors in Scopolamine-induced Amnesia." *J Neurochemistry* 102.6 (2007): 1978-1989. Print.

Bureš, Jan, Federico Bermudez-Rattoni, and Takashi Yamamoto. *Conditioned Taste Aversion: Memory of a Special Kind*. Oxford: Oxford UP, 1998. Print.

Buryanovskyy, Leonid, Yue Fu, Molly Boyd, Yuliang Ma, Tze-chen Hsieh, Joseph M. Wu, and Zhongtao Zhang. "Crystal Structure of Quinone Reductase 2 in Complex with Resveratrol." *Biochemistry* 43.36 (2004): 11417-11426. Print.

Ferry, Gilles, Sabrina Hecht, Sylvie Berger, Natacha Moulharat, Francis Coge, Gérald Guillaumet, Véronique Leclerc, Saïd Yous, Philippe Delagrange, and Jean A. Boutin. "Old and New Inhibitors of Quinone Reductase 2." *Chemico-Biological Interactions* 186.2 (2010): 103-109. Print.

Graves, P. R., J. J. Kwiek, P. Fadden, R. Ray, K. Hardeman, A. M. Coley, M. Foley, and T. A. Haystead. "Discovery of Novel Targets of Quinoline Drugs in the Human Purine Binding Proteome." *Mol Pharmacol* 62 (2002): 1364-372. Print.

Harada, Shoji, Chieko Fujii, Akito Hayashi, and Norio Ohkoshi. "An Association between Idiopathic Parkinson's Disease and Polymorphisms of Phase II Detoxification Enzymes: Glutathione S-Transferase M1 and Quinone Oxidoreductase 1 and 2." *Biochemical and Biophysical Research Communications* 288.4 (2001): 887-92. Print.

Harada, Shoji, Hirokazu Tachikawa, and Yoichi Kawanishi. "A Possible Association between an Insertion/deletion Polymorphism of the NQO2 Gene and Schizophrenia." *Psychiatric Genetics* 13.4 (2003): 205-09. Print.

Hashimoto, Tetsuya, and Masami Nakai. "Increased Hippocampal Quinone Reductase 2 in Alzheimer's Disease." *Neuroscience Letters* 502.1 (2011): 10-12. Print.

Iskander, K. "Deficiency of NRH:Quinone Oxidoreductase 2 Increases Susceptibility to 7,12-Dimethylbenz(a)anthracene and Benzo(a)pyrene-Induced Skin Carcinogenesis." *Cancer Research* 64.17 (2004): 5925-928. Print.

Jaiswal, A. K. "Human NAD(P)H:quinone Oxidoreductase2. Gene Structure, Activity, and Tissue-specific Expression." *J Biol Chem* 269.20 (1994): 14502-4508. Print.

Kwiek, Jesse J., Timothy A. J. Haystead, and Johannes Rudolph. "Kinetic Mechanism of Quinone Oxidoreductase 2 and Its Inhibition by the Antimalarial Quinolines." *Biochemistry* 43.15 (2004): 4538-547. Print.

Lois, C., E. J. Hong, S. Pease, E. J. Brown, and D. Baltimore. "Germline Transmission and Tissue-specific Expression of Transgenes Delivered by Lentiviral Vectors." *Science* 295.5556 (2002): 868-72. Print.

Long, Delwin J., and Anil K. Jaiswal. "NRH:quinone Oxidoreductase2 (NQO2)." *Chemico-Biological Interactions* 129.1-2 (2000): 99-112. Print.

Mailliet, F., G. Ferry, F. Vella, K. Thiam, P. Delagrange, and J. A. Boutin. "Organs from Mice Deleted for NRH:quinone Oxidoreductase 2 Are Deprived of the Melatonin Binding Site MT3." *FEBS Lett* 578 (2004): 116-20. Print.

Mailliet, F., G. Ferry, F. Vella, S. Berger, F. Coge, P. Chomarat, C. Mallet, S. P. Guenin, G. Guillaumet, M. C. Viaud-Massuard, S. Yous, P. Delagrange, and J. A. Boutin. "Characterization of the Melatoninergic MT3 Binding Site on the NRH:quinone Oxidoreductase 2 Enzyme." *Biochem Pharmacol* 71.(1-2) (2005): 74-88. Print.

Meiri, Noam, and Kobi Rosenblum. "Lateral Ventricle Injection of the Protein Synthesis Inhibitor Anisomycin Impairs Long-term Memory in a Spatial Memory Task." *Brain Research* 789.1 (1998): 48-55. Print.

Paxinos, George, and Charles Watson. *The Rat Brain in Stereotaxic Coordinates*. Sydney: Academic, 1986. Print.

"Quinones." *IUPAC Gold Book*—. N.p., n.d. Web. 26 Aug. 2013.

Rosenblum, Kobi. "Conditioned Taste Aversion and Taste Learning: Molecular Mechanisms." *Concise Learning and Memory: The Editor's Selection*. Amsterdam: Academic, 2008. N. pag. Print.

Rosenblum, K., N. Meiri, and Y. Dudai. "Taste Memory: The Role of Protein Synthesis in Gustatory Cortex." *Behavioral and Neural Biology* 59.1 (1993): 49-56. Print.

Rosenblum, K., R. Schull, N. Meiri, Y. R. Hadari, Y. Zick, and Y. Dudai. "Modulation of Protein Tyrosine Phosphorylation in Rat Insular Cortex after Conditioned Taste Aversion Training." *Proceedings of the National Academy of Sciences* 92.4 (1995): 1157-161. Print.

Vella, F., G. Ferry, P. Delagrange, and J. Boutin. "NRH:quinone Reductase 2: An Enzyme of Surprises and Mysteries." *Biochemical Pharmacology* 71.1-2 (2005): 1-12. Print.

Wang, W., and A. Jaiswal. "Sp3 Repression of Polymorphic Human NRH:quinone Oxidoreductase 2 Gene Promoter." *Free Radical Biology and Medicine* 37.8 (2004): 1231-243. Print.

Vorhees, C. V., and Williams, M. T., "Morris water maze: procedures for assessing spatial and related forms of learning and memory." *Nat Protoc.*, 1(2), (2006): 848-58.

What is claimed is:

1. A pharmaceutical composition, comprising a shRNA molecule having a sequence corresponding to SEQ ID NO: 2, 3 or 4, or a vector comprising said shRNA molecule or a nucleic acid molecule encoding said shRNA molecule, and a pharmaceutically acceptable carrier.

2. The pharmaceutical composition of claim 1, wherein said vector is a modified virus derived from a virus selected from retrovirus, adenovirus, adeno-associated virus, pox virus, alphavirus, herpes virus, or lentivirus.

3. The pharmaceutical composition of claim 2, wherein said vector is a modified lentivirus.

4. A pharmaceutical composition, comprising (a) a vector comprising a shRNA molecule having a sequence corresponding to SEQ ID NO: 2, 3 or 4 or a nucleic acid molecule encoding said shRNA molecule, and (b) a pharmaceutically acceptable carrier.

5. The pharmaceutical composition of claim 4, wherein said vector is a modified virus derived from a virus selected from retrovirus, adenovirus, adeno-associated virus, pox virus, alphavirus, herpes virus, or lentivirus.

6. The pharmaceutical composition of claim 5, wherein said vector is a modified lentivirus.

* * * * *

SEQUENCE LISTING

```
<160> NUMBER OF SEQ ID NOS: 7

<210> SEQ ID NO 1
<211> LENGTH: 1139
<212> TYPE: DNA
<213> ORGANISM: Homo sapiens

<400> SEQUENCE: 1
gggcggggcc tcggcgtggt aggcgcgctg cgtaaagagg cctgcagtcc cgcggcgcgg      60
ggcaggttcc gggctgctta ggttggcacc ggtccgtggt ccccgggggc gcagtcgcag     120
```

| | | |
|---|---|---|
| cgctcccgcc ctccaggcgt cagcgagtgc gcggtccagt gcggccggaa cctggcgcaa | 180 | |
| ctcctagagc ggtccttggg gagacgcggg tcccagtcct gcggctccta ctggggagtg | 240 | |
| cgctggtcgg aagattgctg gactcgctga agagagacta cgcaggaaag ccccagccac | 300 | |
| ccatcaaatc agagagaagg aatccacctt cttacgctat ggcaggtaag aaagtactca | 360 | |
| ttgtctatgc acaccaggaa cccaagtctt tcaacggatc cttgaagaat gtggctgtag | 420 | |
| atgaactgag caggcagggc tgcaccgtca cagtgtctga tttgtatgcc atgaaccttg | 480 | |
| agccgagggc cacagacaaa gatatcactg gtactctttc taatcctgag gttttcaatt | 540 | |
| atggagtgga aacccacgaa gcctacaagc aaaggtctct ggctagcgac atcactgatg | 600 | |
| agcagaaaaa ggttcgggag gctgacctag tgatatttca gttcccgctg tactggttca | 660 | |
| gcgtgccagc catcctgaag ggctggatgg atagggtgct gtgccagggc tttgcctttg | 720 | |
| acatcccagg attctacgat tccggtttgc tccagggtaa actagcgctc ctttccgtaa | 780 | |
| ccacgggagg cacggccgag atgtacacga agacaggagt caatggagat tctcgatact | 840 | |
| tcctgtggcc actccagcat ggcacattac acttctgtgg atttaaagtc cttgcccctc | 900 | |
| agatcagctt tgctcctgaa attgcatccg aagaagaaag aaaggggatg gtggctgcgt | 960 | |
| ggtcccagag gctgcagacc atctggaagg aagagcccat cccctgcaca gcccactggc | 1020 | |
| acttcgggca ataactctgt ggcacgtggg catcacgtaa gcagcacact aggaggccca | 1080 | |
| ggcgcaggca aagagaagat ggtgctgtca tgaaataaaa ttacaacata gctacctgg | 1139 | |

```
<210> SEQ ID NO 2
<211> LENGTH: 58
<212> TYPE: RNA
<213> ORGANISM: Artificial Sequence
<220> FEATURE:
<223> OTHER INFORMATION: synthetic

<400> SEQUENCE: 2
ccgggaggcu gaccuaguga uauuucucga gaaauaucac uaggucagcc ucuuuug      58

<210> SEQ ID NO 3
<211> LENGTH: 58
<212> TYPE: RNA
<213> ORGANISM: Artificial Sequence
<220> FEATURE:
<223> OTHER INFORMATION: synthetic

<400> SEQUENCE: 3
ccgggaggcu gaccuaguga uauuucucga gaaauaucac uaggucagcc ucuuuug      58

<210> SEQ ID NO 4
<211> LENGTH: 58
<212> TYPE: RNA
<213> ORGANISM: Artificial Sequence
<220> FEATURE:
<223> OTHER INFORMATION: synthetic

<400> SEQUENCE: 4
ccggccacuc cagcauggca cauuacucga guaaugugcc augcuggagu gguuuug      58

<210> SEQ ID NO 5
<211> LENGTH: 58
<212> TYPE: RNA
<213> ORGANISM: Artificial Sequence
<220> FEATURE:
<223> OTHER INFORMATION: synthetic

<400> SEQUENCE: 5
```

-continued

```
ccggccacua uacugguuca gcguucucga gaacgcugaa ccaguauagu gguuuuug        58

<210> SEQ ID NO 6
<211> LENGTH: 58
<212> TYPE: RNA
<213> ORGANISM: Artificial Sequence
<220> FEATURE:
<223> OTHER INFORMATION: synthetic

<400> SEQUENCE: 6
ccggcaguca cugugucuga uuuaucucga gauaaaucag acacagugac uguuuuug        58

<210> SEQ ID NO 7
<211> LENGTH: 58
<212> TYPE: RNA
<213> ORGANISM: Artificial Sequence
<220> FEATURE:
<223> OTHER INFORMATION: synthetic

<400> SEQUENCE: 7
ccggagcucu gaccagugau auauucucga gaauauauca cuggucagag cuuuuug         58
```